(12) United States Patent
Cahill

(10) Patent No.: US 10,349,984 B2
(45) Date of Patent: Jul. 16, 2019

(54) MULTI-MODE TORQUE DRIVERS EMPLOYING ANTI-BACKDRIVE UNITS FOR MANAGING PEDICLE SCREW ATTACHMENTS WITH VERTEBRAE, AND RELATED SYSTEMS AND METHODS

(71) Applicant: Kevin S. Cahill, Charlotte, NC (US)

(72) Inventor: Kevin S. Cahill, Charlotte, NC (US)

(73) Assignee: Power T Handle, LLC, Wilmington, NC (US)

( * ) Notice: Subject to any disclaimer, the term of this patent is extended or adjusted under 35 U.S.C. 154(b) by 678 days.

(21) Appl. No.: 14/757,804

(22) Filed: Dec. 23, 2015

(65) Prior Publication Data
US 2017/0181774 A1 Jun. 29, 2017

(51) Int. Cl.
*A61B 17/70* (2006.01)
*A61B 17/88* (2006.01)
*B25B 15/02* (2006.01)
*B25B 21/00* (2006.01)
*A61B 17/00* (2006.01)

(52) U.S. Cl.
CPC ...... *A61B 17/7079* (2013.01); *A61B 17/7082* (2013.01); *A61B 17/8875* (2013.01); *B25B 15/02* (2013.01); *B25B 21/00* (2013.01); *A61B 2017/0042* (2013.01); *A61B 2017/00398* (2013.01); *A61B 2017/00407* (2013.01); *A61B 2017/00411* (2013.01); *A61B 2017/00424* (2013.01)

(58) Field of Classification Search
CPC .......................... A61B 17/8875; A61B 17/1628
See application file for complete search history.

(56) References Cited

U.S. PATENT DOCUMENTS

| 3,802,518 A | * | 4/1974 | Albert | B25B 13/46 173/217 |
| 4,078,589 A | * | 3/1978 | Miller | B25B 21/00 310/50 |
| D287,814 S | * | 1/1987 | Hiraishi | D8/67 |

(Continued)

OTHER PUBLICATIONS

International Search Report and Written Opinion, PCT/US2016/068150, dated May 4, 2017.

(Continued)

*Primary Examiner* — David W Bates
(74) *Attorney, Agent, or Firm* — Stephen R. Bylciw, Esq.

(57) ABSTRACT

Multi-mode torque drivers employing anti-backdrive units for managing pedicle screw attachments with vertebrae, and related systems and methods are disclosed. A spinal column includes vertebrae in an articulating structure protecting a spinal cord. Medical intervention may involve limiting the relative motion between vertebrae by fusing vertebrae together with mechanical assemblies, including pedicle screws attached to the vertebrae. A torque driver may be used to form the pedicle screw attachments with vertebrae. By including an anti-backdrive unit and a motor assembly enclosed within a handle body as part of a multi-mode torque driver, the user may apply sequential combinations of manual and motorized torques to the screws with high levels of tactile feedback as desired. In this manner, pedicle screw attachments may be efficiently achieved with fewer injuries to the patient and surgeon while minimizing screw attachment failures.

24 Claims, 18 Drawing Sheets

(56) References Cited

U.S. PATENT DOCUMENTS

| | | | |
|---|---|---|---|
| 4,754,669 A * | 7/1988 | Verdier | B25B 21/00 81/57.14 |
| 5,016,501 A | 5/1991 | Holzer, Jr. | |
| 5,788,021 A * | 8/1998 | Tsai | B25B 21/00 188/67 |
| 6,151,998 A * | 11/2000 | Fu-Hui | B25G 1/085 81/177.1 |
| 6,220,368 B1 * | 4/2001 | Ark | A61B 17/1626 173/170 |
| 6,273,200 B1 * | 8/2001 | Smith | B25B 21/00 173/216 |
| 7,048,107 B1 | 5/2006 | Geis et al. | |
| D557,584 S * | 12/2007 | Gao | D8/107 |
| D613,144 S * | 4/2010 | Lin | D8/107 |
| 8,104,145 B1 * | 1/2012 | Hajianpour | A01K 27/008 119/772 |
| D654,589 S * | 2/2012 | Bast | D24/133 |
| 8,651,198 B2 * | 2/2014 | Ito | B25B 21/02 173/109 |
| 2007/0132196 A1 * | 6/2007 | Puzio | B23B 31/1253 279/2.21 |
| 2009/0299439 A1 | 12/2009 | Mire et al. | |
| 2010/0179560 A1 | 7/2010 | Chenaux | |
| 2012/0046665 A1 * | 2/2012 | Kim | A61B 17/7082 606/104 |
| 2012/0109143 A1 * | 5/2012 | Steele | A61B 17/7082 606/104 |
| 2017/0348037 A1 * | 12/2017 | Sexson | A61B 17/1626 |

OTHER PUBLICATIONS

"Black & Decker Gyro Screwdriver—M3 Design Product Teardown," M3 Design, (downloaded from Internet at: cdn1.m3design.com/wordpress/wp-content/uploads/2014/09/M3-Teardown-Black-Decker-Gyro-Screwdriver.pdf), dated Sep. 2014.

* cited by examiner

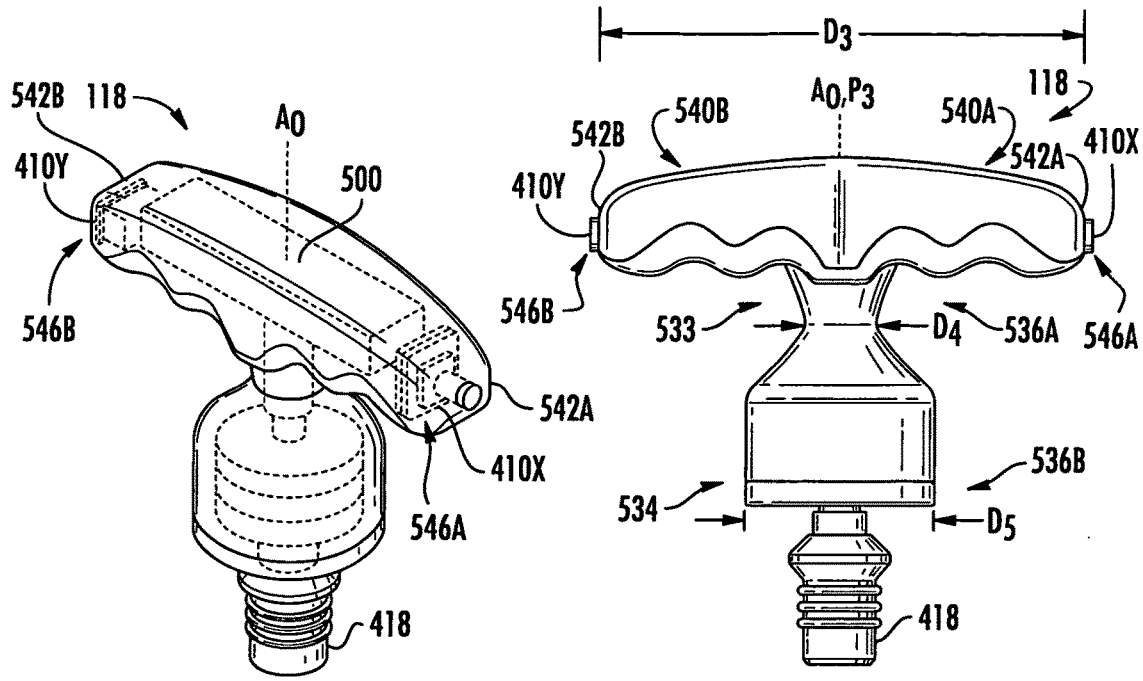
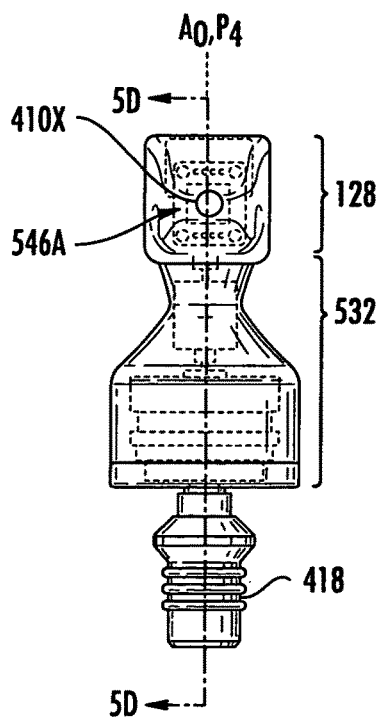
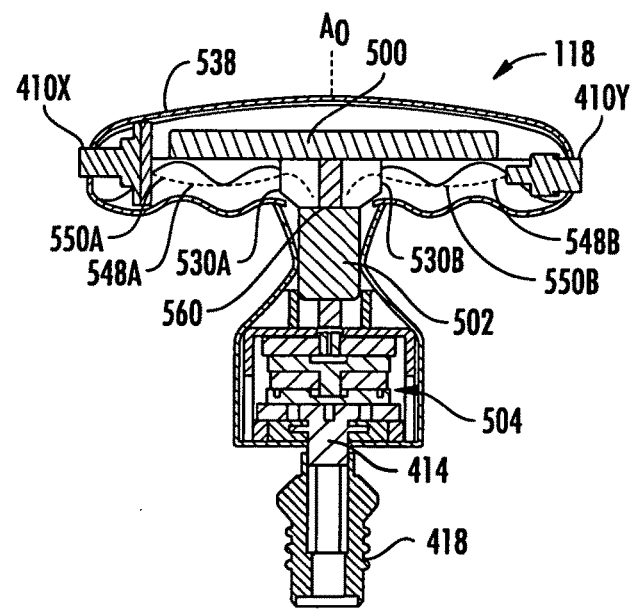
FIG. 5A
FIG. 5B
FIG. 5C
FIG. 5D

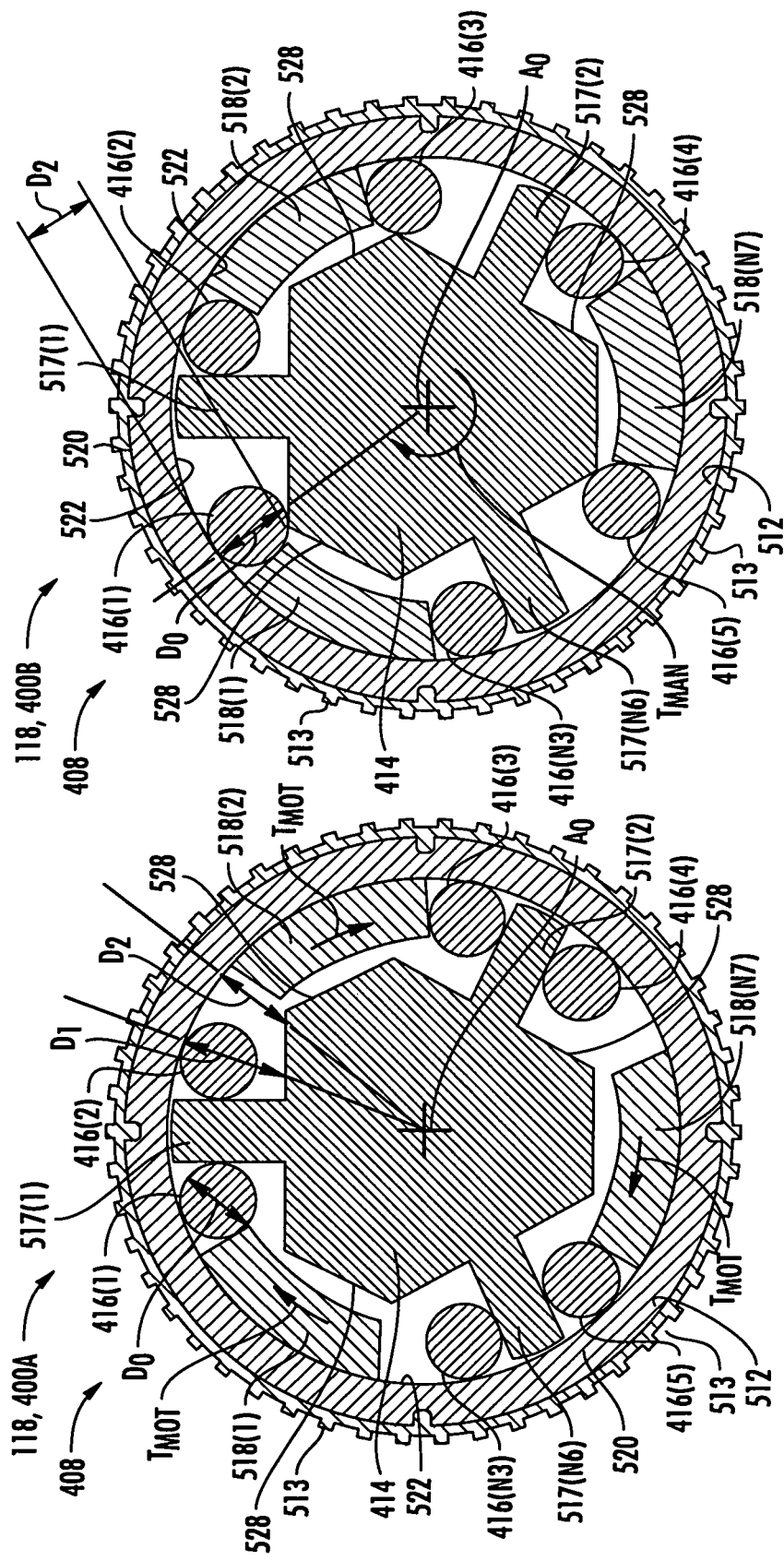

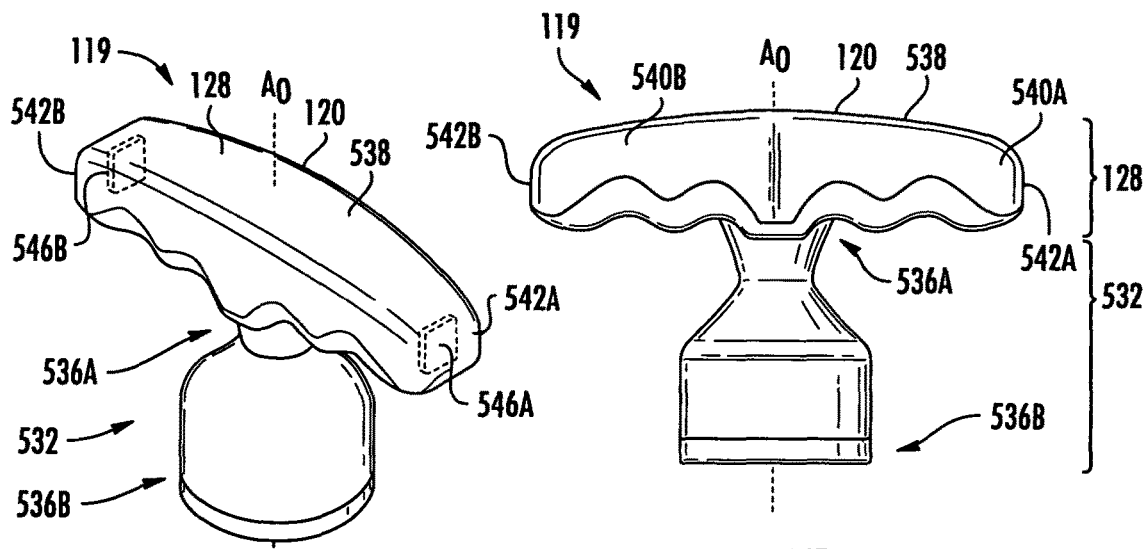
FIG. 7A
FIG. 7B
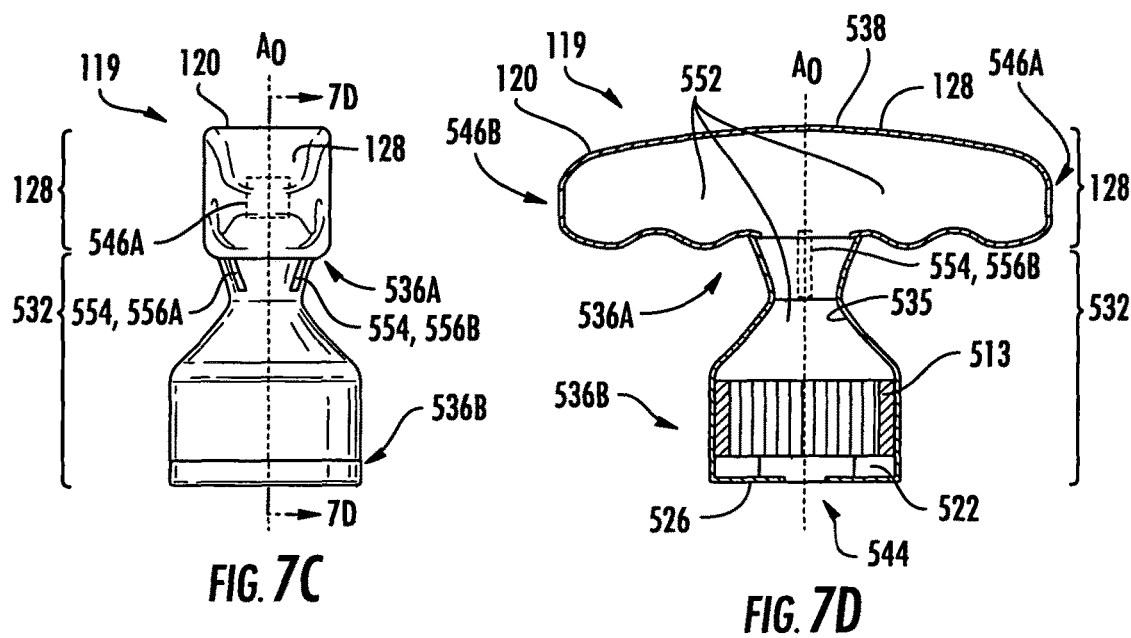
FIG. 7C
FIG. 7D

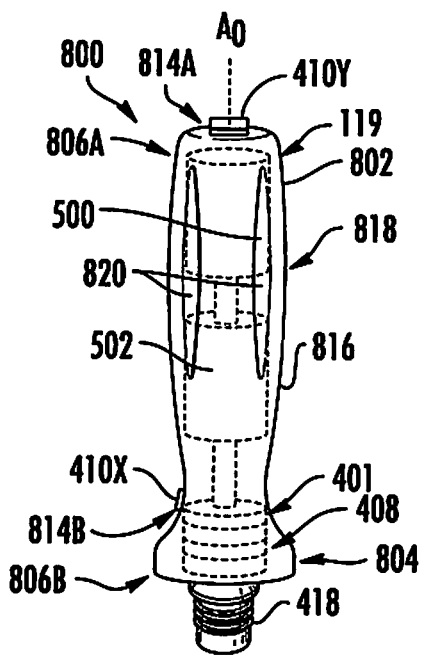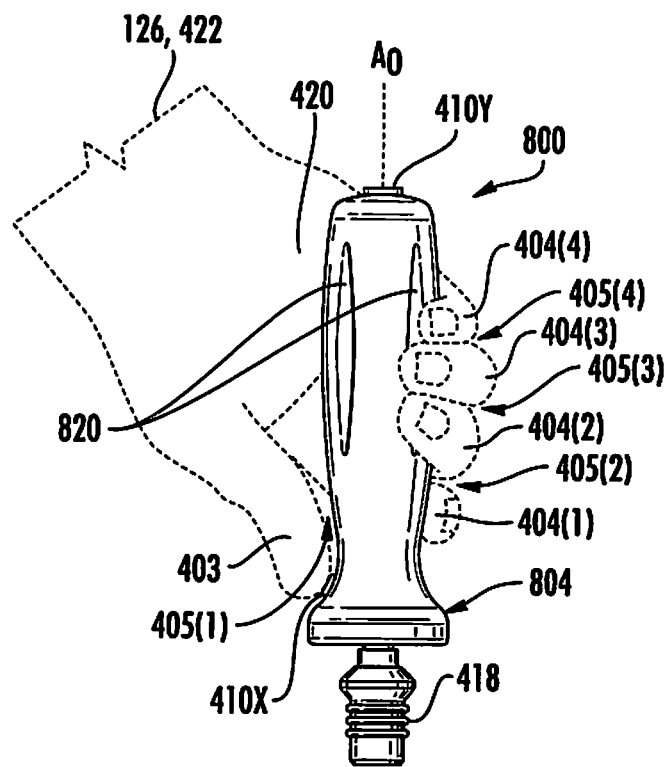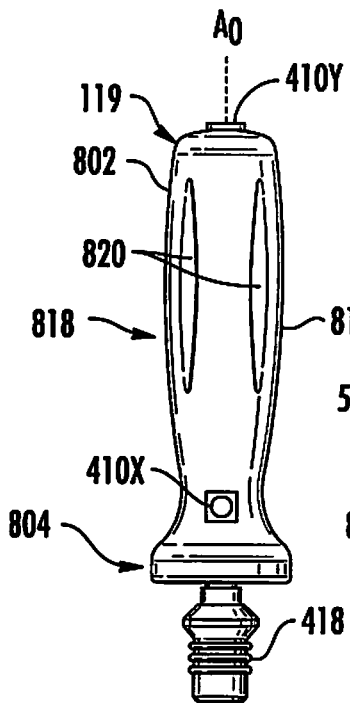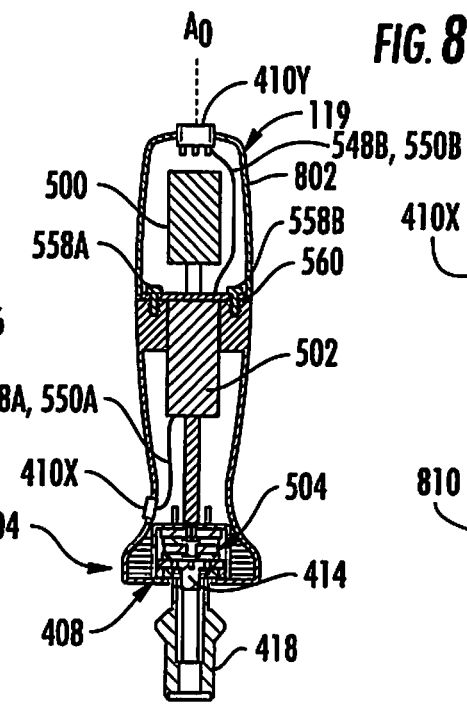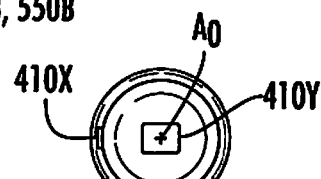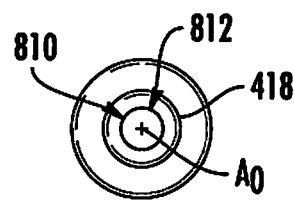
FIG. 8A
FIG. 8B
FIG. 8C
FIG. 8D
FIG. 8E
FIG. 8F

MULTI-MODE TORQUE DRIVERS EMPLOYING ANTI-BACKDRIVE UNITS FOR MANAGING PEDICLE SCREW ATTACHMENTS WITH VERTEBRAE, AND RELATED SYSTEMS AND METHODS

BACKGROUND

Field of the Disclosure

The technology of the disclosure relates to surgical screwdriver devices and related assemblies and methods for creating and removing pedicle screw attachments with vertebrae.

Technical Background

A vertebral column and a spinal cord of a patient extend from the skull to the pelvis and form a longitudinal axis of a patient. The column includes vertebra that are separated by fibrocartilage structures (intervertebral disks) that are interconnected with ligaments. The vertebral column protects the spinal cord and provides structural support for the patient. The spinal cord along with a bundle of nerve fibers extending from the spinal cord form a central nervous system enabling communication between the brain and other parts of the body of the patient. The spinal cord is protected by being disposed through a vertebral canal formed by openings in each of the vertebrae. The vertebral column typically facilitates movement of the patient by enabling relative movement between adjacent vertebrae and often serves its functions without issues.

Abnormalities may occur to the vertebral column necessitating medical intervention. In one example, one or more portions of the vertebral column may have abnormalities from development issues and/or trauma making relative movement at these locations problematic. Medical intervention may be necessary to stop relative movement at these locations. Types of exemplary abnormalities include degenerative disc disease, spondylolisthesis, trauma, deformities, tumors, stenosis, and pseudoarthrosis (earlier failed spine surgery). Pain may be lessened and/or opportunities for healing may occur once relative movement is prevented.

Conventional spine fusion is one surgical approach for permanently or temporarily immobilizing adjacent vertebrae relative to each other. In this approach, fasteners (e.g., pedicle screws) are attached to the adjacent vertebrae to serve as anchor points, and these anchor points are interconnected with at least one immobilizing rod to stop relative movement between the adjacent vertebrae. Conventionally an attending surgeon typically attaches the pedicle screws to the vertebrae by screwing these pedicle screws into the adjacent vertebrae with a surgical screwdriver. The desired trajectory of each screw into the desired vertebra is carefully selected to avoid damage to the spinal cord and nerve fibers extending therefrom between vertebrae. The desired trajectory is also selected to achieve a stable and strong attachment between the screw and the vertebrae. The advantage to achieving a strong pedicle screw attachment to the vertebra is that the adjacent vertebrae are immobilized with respect to each other when the interconnection rod is connected to the pedicle screws.

Inserting and retracting the pedicle screw into and from the vertebrae is difficult, because it is a physically demanding task for the surgeon and requires precision to avoid inflicting nerve injuries to the patient. Specifically, surgeons have traditionally utilized manual screwdrivers to ensure that the screws are inserted precisely along the desired trajectory and that the final position of the screw results in a strong attachment. The proximity of the desired trajectory of the pedicle screw to the spinal cord and spinal nerves makes it imperative to precisely follow the desired trajectory and the manual screwdrivers can provide the precision and heightened feedback desired by the surgeon.

The manual screwdriver also requires the surgeon to manually apply a relatively high torque, which when applied, can be easily monitored by the surgeon to understand whether a strong pedicle screw attachment has been achieved. However, manually applying a high torque to gain precision is gained at the expense of repetitive motion injuries (e.g., lateral epicondylitis) suffered by many attending surgeons.

Attempts have been made to reduce surgeon fatigue and injury by replacing the manual screwdrivers used for pedicle screw insertion with power screwdrivers developed for use in the building construction industry and modified to have higher torque to insert pedicle screws into vertebrae. Although the objective of power screwdrivers may have reduced surgeon fatigue and the likelihood of repetitive use injuries, these power screwdrivers offer less sensitive tactile feedback to the surgeon during screw insertion than with manual surgical screwdrivers. In some cases users have reported "zero feel" as to feedback regarding the strength of the pedicle screw attachment when using the power screwdrivers. Thus, conventional power screwdrivers used with pedicle screws have merely become power screwdrivers from the building construction industry modified for surgery without meeting special medical requirements. The end result is that it is difficult with power screwdrivers originally designed for the building construction industry to ensure that the pedicle screw attachment with the vertebra is strong and stable and that injury to the patient is avoided. Similar challenges occur if and when the pedicle screw is removed from the vertebra. Accordingly new approaches are needed to manage pedicle screw attachments with vertebra, so that strong and stable attachments are achieved without injury to patients and surgeons.

SUMMARY OF THE DETAILED DESCRIPTION

Embodiments disclosed herein include multi-mode torque drivers employing anti-backdrive units for managing pedicle screw attachments with vertebrae, and related systems and methods. A spinal column includes vertebrae in an articulating structure protecting a spinal cord. Medical intervention may involve limiting the relative motion between vertebrae by fusing vertebrae together with mechanical assemblies, including pedicle screws attached to the vertebrae. A multi-mode torque driver may be used to form the pedicle screw attachments with vertebrae. By including an anti-backdrive unit and a motor assembly enclosed within a handle body as part of a multi-mode torque driver, the user may apply sequential combinations of manual and motorized torques to the screws with high levels of tactile feedback as desired. In this manner, pedicle screw attachments may be efficiently achieved with fewer injuries to the patient and surgeon while minimizing screw attachment failures.

In one embodiment, a T-shaped body of a multi-mode torque driver for managing a pedicle screw attachment with a vertebra is disclosed. The T-shaped body includes center portion extending along an output rotational axis from a first end to a second end, wherein the center portion is arranged to transfer a manual torque from the first end to the second end. The T-shaped body further includes a gripper handle portion formed as a plurality of protrusions attached to and extending from the first end of the center portion to respective distal ends disposed away from the output rotational axis. The protrusions are adapted to receive and transfer the manual torque from a user to the first end of the center portion. The gripper handle portion is shaped for adjacent fingers of a hand of the user to wrap around respective ones of the plurality of protrusions as the center portion and the output rotational axis are disposed within an interdigital space between the adjacent fingers when the gripper handle receives the manual torque from the user in a manual mode. The T-shaped body further includes an inner surface forming an inner space connecting at least one motor control port at the gripper handle portion to an output opening at the second end, wherein the inner surface includes an electric motor mounting interface configured to receive a motorized torque when in a power mode. In this manner, the user can efficiently provide motorized torque in a power mode, and precisely provide manual torque and valuable levels of tactile feedback in the manual mode.

In another embodiment, a multi-mode torque driver for managing a pedicle screw attachment with a vertebra is disclosed. The multi-mode torque driver includes a handle body extending along an output rotational axis from a first end to a second end. The handle body including having an inner surface forming an inner space connecting at least one motor control port to an output opening at the second end. The multi-mode torque driver also includes a motor assembly disposed within the inner space. The multi-mode torque driver further includes an anti-backdrive unit coupled to the motor assembly and including an output element disposed through the output opening and at least one locking element disposed within the inner space. The multi-mode torque driver further includes upon the anti-backdrive unit receiving a motorized torque from the motor assembly in the power mode, the least one locking element abuts against the output element and an output interface of the motor assembly to transmit the motorized torque to the output element as a system torque. The multi-mode torque driver is further configured upon a manual torque being applied to the handle body by a single hand of a user while the output element is coupled to the pedicle screw and the output element is free from the motorized torque, then at least one locking element is disposed to automatically lock the output element relative to the handle body and transmit the manual torque from the handle body to the output element as the system torque in a manual mode. In this manner, spinal surgeries can be completed in a shorter time while ensuring that pedicle screw attachments are created that are strong and stable over time while avoiding injury to the patient and surgeon.

In another embodiment, a method is disclosed for managing a pedicle screw attachment with a vertebra. This method may include transmitting, with an output element of an anti-backdrive unit disposed within a handle body of a multi-mode torque driver, the system torque from the output element to the pedicle screw, wherein the system torque includes a manual torque during a manual mode and a motorized torque during a power mode, wherein the system torque moves the pedicle screw relative to the vertebra. The method may further include generating, with a motor assembly disposed within the handle body, the motorized torque during the power mode and transmitting the motorized torque to the anti-backdrive unit with an output interface of the motor assembly in the power mode. The method may further include upon applying the manual torque to the handle body with a single hand of a user while the output element is coupled to the pedicle screw and the output element is free from the motorized torque, automatically locking the output element in the manual mode relative to the handle body with at least one locking element of the anti-backdrive unit and transmitting the manual torque from the handle body to the output element in the manual mode. In this manner, immobilization systems including pedicle screw attachments are formed more efficiently to minimize surgical times that when occurring with shorter durations may reduce infection rates or other complications for patients.

Additional features and advantages will be set forth in the detailed description which follows, and in part will be readily apparent to those skilled in the art from that description or recognized by practicing the embodiments as described herein, including the detailed description that follows, the claims, as well as the appended drawings.

It is to be understood that both the foregoing general description and the following detailed description present embodiments, and are intended to provide an overview or framework for understanding the nature and character of the disclosure. The accompanying drawings are included to provide a further understanding, and are incorporated into and constitute a part of this specification. The drawings illustrate various embodiments, and together with the description serve to explain the principles and operation of the concepts disclosed.

BRIEF DESCRIPTION OF THE FIGURES

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

FIGS. 4E-1 and 4E-2 are exemplary graphs of system torque produced by the multi-mode torque driver of FIG. 4A and resistance torque provided to the multi-mode torque driver, respectively, over an exemplary second time period during the power and manual modes illustrating the resistance torque temporarily below the resistance threshold;

FIGS. 5A through 5G are a top perspective view, front view, right side view, partial front view, top view, bottom view, and exploded view, respectively, of the multi-mode torque driver of the pedicle screw system of FIG. 1B, wherein the handle body in this depicted embodiment is a T-shaped body;

FIGS. 6A and 6B are partial top sectional views parallel to the output rotational axis of the multi-mode torque driver in FIGS. 4A and 4B, respectively, illustrating the anti-backdrive unit operating in the power and manual modes;

FIGS. 7A through 7F are a top perspective view, front view, right side view, partial front sectional view, top view, and bottom view, respectively, of the T-shaped body of the multi-mode torque driver of the pedicle screw system of FIG. 1B;

FIGS. 8A through 8G are a top perspective view, front view, left side view, sectional front view, top view, bottom view, and exploded view, respectively, of a second exemplary embodiment of a multi-mode torque driver compatible with the screw interface of FIG. 1B, wherein a handle body in this second embodiment is an axially-shaped body with a flared end;

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Reference will now be made in detail to the embodiments, examples of which are illustrated in the accompanying drawings, in which some, but not all embodiments are shown. Indeed, the concepts may be embodied in many different forms and should not be construed as limiting herein; rather, these embodiments are provided so that this disclosure will satisfy applicable legal requirements. Whenever possible, like reference numbers will be used to refer to like components or parts.

Embodiments disclosed herein include multi-mode torque drivers employing anti-backdrive units for managing pedicle screw attachments with vertebrae, and related systems and methods. A spinal column includes vertebrae in an articulating structure protecting a spinal cord. Medical intervention may involve limiting the relative motion between vertebrae by fusing vertebrae together with mechanical assemblies, including pedicle screws attached to the vertebrae. A torque driver may be used to form the pedicle screw attachments with vertebrae. By including an anti-backdrive unit and a motor assembly enclosed within a handle body as part of a multi-mode torque driver, the user may apply sequential combinations of manual and motorized torques to the screws with high levels of tactile feedback as desired. In this manner, pedicle screw attachments may be efficiently achieved with fewer injuries to the patient and surgeon while minimizing screw attachment failures.

Figure 1A:
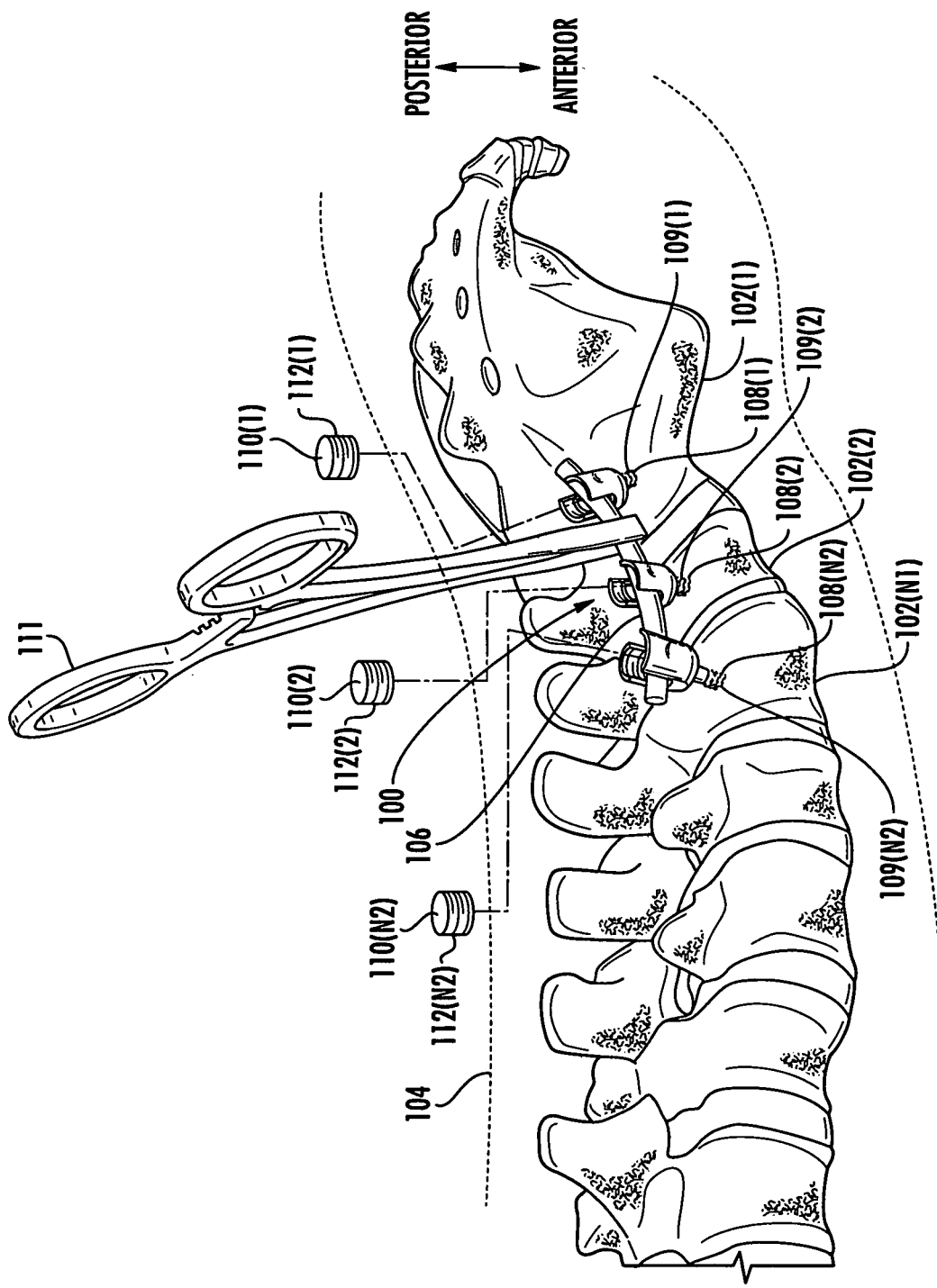
FIG. 1A illustrates partially exploded posterior perspective view of an exemplary immobilization system being attached to vertebrae of a patient, wherein the system includes an immobilization rod, pedicle screws, and secondary fasteners.

In this regard, FIG. 1A illustrates partially exploded posterior perspective view of an immobilization system 100 being attached to vertebrae 102(1)-102(N1) of a patient 104, to immobilize (or "fuse") the vertebrae 102(1)-102(N1) relative to each other. The immobilization system 100 includes various components to be discussed below such as an immobilization rod 106, pedicle screws 108(1)-108(N2), and secondary fasteners 110(1)-110(N2). When completed, the immobilization system 100 may be used to immobilize (or "fuse") the vertebrae 102(1)-102(N1) of a patient 104 relative to each other. Immobilizing the vertebrate 102(1)-102(N1) with the immobilization system 100 is one medical approach to treat abnormalities that the patient 104 may experience, for example, degenerative disc disease, spondylolisthesis, trauma, deformities, tumors, stenosis, and pseudoarthrosis. The immobilization may offer one or more benefits for the patient 104 including pain reduction, improved healing, and structural support for an improved quality of life. Various quantities of the vertebrae 102(1)-102(N1) may be immobilized depending upon the needs of the patient 104 to provide the optimal benefit. The human spinal cord has over twenty different articulating vertebrae and various combinations of these may be connected to an immobilization system 100. For purposes of illustration, some embodiments (not shown) of the immobilization system 100 may include two pedicle screws to be attached to each vertebrae, and so, if all twenty-four articulating vertebrae of the human patient were to be fused, then forty-eight pedicle screw attachments would be required. The efficiency and strain on the surgeon may become increasingly important in these larger quantity pedicle screw situations, because the higher quantities may wear down the ability of the surgeon to precisely turn the pedicle screws 108(1)-108(N2) for managing the pedicle screw attachments 109(1)-109(N2) with the vertebrae 102(1)-102(N1).

The immobilization system 100 includes components that collectively form a rigid mechanical assembly, which when anchored to the vertebrae 102(1)-102(N1), cause the vertebrae 102(1)-102(N1) to be immobilized to each other. Immobilization includes the pedicle screws 108(1)-108(N2) being inserted into the vertebrae 102(1)-102(N1) to rigidly fix the pedicle screws 108(1)-108(N2) relative to the vertebrae 102(1)-102(N1) to form pedicle screw attachments 109(1)-109(N2) between the immobilization system 100 and the vertebrae 102(1)-102(N1). Also, the immobilization rod 106 of the immobilization system 100 is rigidly secured to the pedicle screws 108(1)-108(N2) and may be placed in abutment using placement means (e.g., forceps 111). Once the immobilization rod 106 is in abutment, the secondary fasteners 110(1)-110(N2) rigidly secure the immobilization rod 106 to the pedicle screws 108(1)-108(N2), for example, by engaging male threads 112(1)-112(N2) of the secondary fasteners 110(1)-110(N) with female threads 114(1)-114(N2) of the pedicle screws 108(1)-108(N2). This engagement causes the immobilization rod 106 to be clamped securely to the pedicle screws 108(1)-108(N2) to form the rigid attachment. In this manner, the vertebrae 102(1)-102(N1) may be immobilized relative to each other when the immobilization system 100 is fully implemented within the patient 104.

Figure 1B:
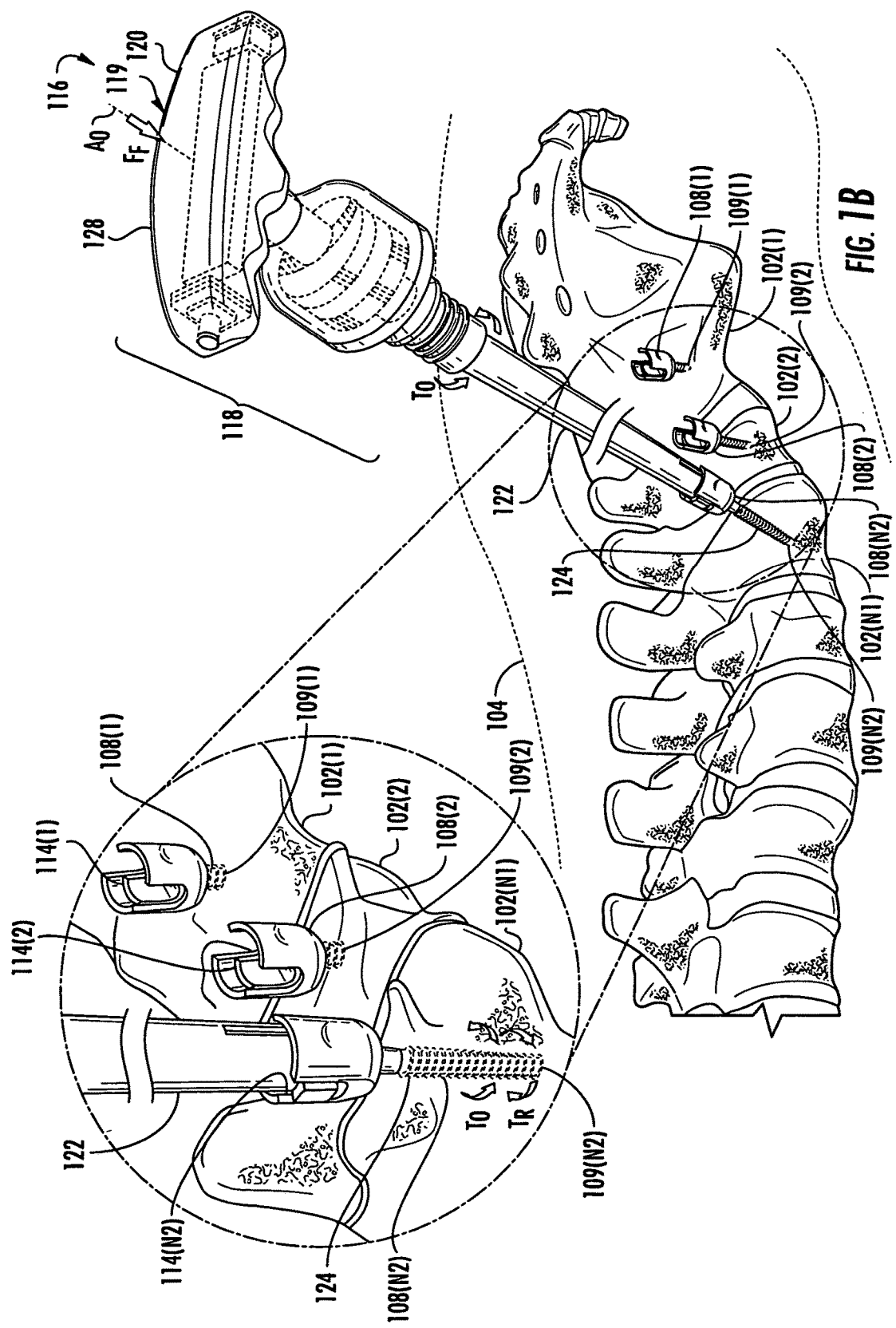
FIG. 1B is a partial posterior perspective view with a close-up view of an exemplary pedicle screw system including a screw interface and an exemplary multi-mode torque driver with an exemplary handle body being used to insert the pedicle screws of FIG. 1A into the vertebrae of the patient to form a pedicle screw attachment.

FIG. 1B is a partial posterior perspective view with a close-up view of an exemplary pedicle screw system 116 including an exemplary multi-mode torque driver 118 employing an exemplary handle body 119 being used to insert the pedicle screws 108(1)-108(2) of FIG. 1A into the vertebrae 102(1)-102(N1) of the patient 104 as part of creating the immobilization system 100 of FIG. 1A. In one embodiment, the handle body 119 may be a T-shaped body 120 as depicted in FIG. 1B. The pedicle screw system 116 includes the multi-mode torque driver 118, a screw interface 122, which may all be coupled and later uncoupled to each other. The multi-mode torque driver 118 generates a system torque T0 configured to be transmitted through the screw interface 122. The screw interface 122 may be coupled and later uncoupled to one of the pedicle screws 108(1)-108 (N2), so that the screw interface 122 transfers the system torque T0 to the pedicle screw 108(1)-108(N2) along the output rotational axis A0 of the pedicle screw system 116. The output rotational axis A0 may or may not be aligned with a longitudinal axis A4 of the pedicle screw 108(N2). In this manner, the system torque T0 may be applied to the pedicle screw 108(N2).

The system torque T0 is used to manage the pedicle screw attachment to the vertebra 102(N1). Specifically, the system torque T0 applied to the pedicle screws 108(1)-108(N2) from the screw interface 122 causes the pedicle screws 108(1)-108(N2) to turn along the output rotational axis A0 and engage the male threads 124 of the pedicle screws 108(1)-108(N2) in abutment with the vertebrae 102(1)-102 (N1). The male threads 124 of each of the pedicle screws 108(1)-108(N2) are disposed at one or more insertion angles that are within a range from parallel to orthogonal to the output rotational axis A0. Accordingly, this engagement of the male threads 124 of the pedicle screws 108(1)-108(N2) with the vertebrae 102(1)-102(N1) during application of the system torque T0 causes the pedicle screws 108(1)-108(N2) to be inserted into the vertebrae 102(1)-102(N1) or retracted from the vertebrae 102(1)-102(N1) depending on a direction of the system torque either in the clockwise or counterclockwise direction. When the pedicle screw turns in a direction to be inserted into the vertebra 102(N1), then a pedicle screw attachment 109(N2) may be formed as the male thread 124 engages with the vertebra 102(N1). Alternatively, the pedicle screw attachment 109(N2) may be removed as the male thread 124 is turned in the opposite direction and the pedicle screw 108(N2) is retracted from the vertebra 102(N1). The pedicle screw attachment 109(N2) is based on at least one of friction and mechanical interference between the male thread 124 and the vertebra 102(N1) resulting in a resistance torque $T_R$ that opposes the system torque T0 applied from the multi-mode torque driver 118. In these situations, the pedicle screw attachment 109(N2) is managed to meet the needs of either establishing or removing the immobilization system 100.

A user 126 (e.g., medical surgeon) supports the pedicle screw system 116 during insertion or retraction of the pedicle screw 108(N2). The user 126 of the pedicle screw system 116 with the T-shaped body 120 may support the pedicle screw system 116 at a gripper handle portion 128 of the pedicle screw system 116, where the user 126 may apply a feed force $F_F$ to the pedicle screw system 116. This feed force $F_F$ may act in combination with the system torque T0 to assist the insertion of the pedicle screws 108(1)-108(N2) into the vertebrae 102(1)-102(N1).

The immobilization system 100 may be disposed within the patient permanently or for an extended length of time. Accordingly, the components of the immobilization system 100 may be made of a strong and medically inert material (e.g, stainless steel) that can remain in the patient 104 without significant corrosion or decrease in strength over time. The secondary fasteners 110(1)-110(N2) may be designed to conventionally lock so that the rigid attachment between the pedicle screws 108(1)-108(N2) and the immobilization rod 106 may remain strong and stable over time. Also, the pedicle screws 108(1)-108(N2) are carefully inserted into the vertebrae 102(1)-102(N1) along a desired trajectory A1 selected and monitored by the user 126 to minimize the opportunity for a later failure of the pedicle screw attachments 109(1)-109(N2) with the vertebra 102 (1)-102(N1) or other injury to the patient 104. Details of the insertion of the pedicle screws 108(1)-108(N2) are now provided with a discussion of the significance of the respective desired trajectory A1 of the pedicle screws 108(1)-108 (N2) before discussing features of the pedicle screw system 116 used to guide the pedicle screws 108(1)-108(N2) along this desired trajectory A1.

Figure 2A:
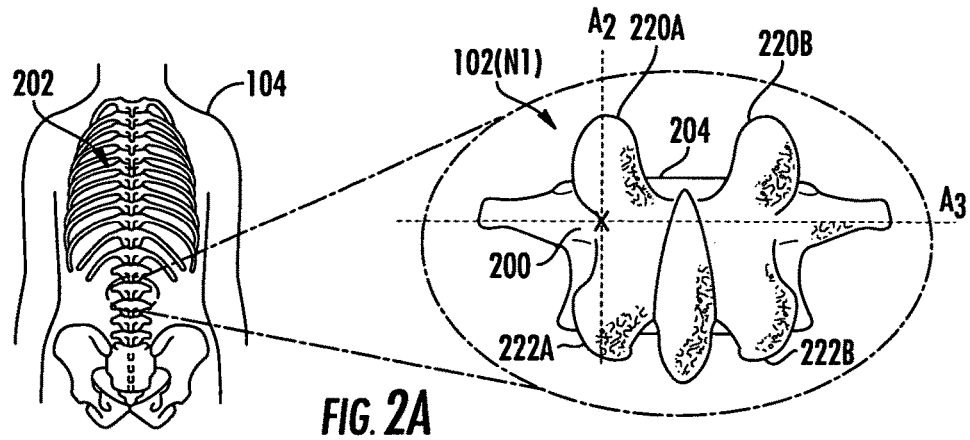
FIGS. 2A through 2C are a posterior close-up view, a left lateral view, and a superior view, respectively, of one of the vertebrae of FIG. 1A illustrating, as is known in the art, an insertion point of a desired trajectory of the respective pedicle screw of FIG. 1A without the respective pedicle screw inserted.
Figure 2B:
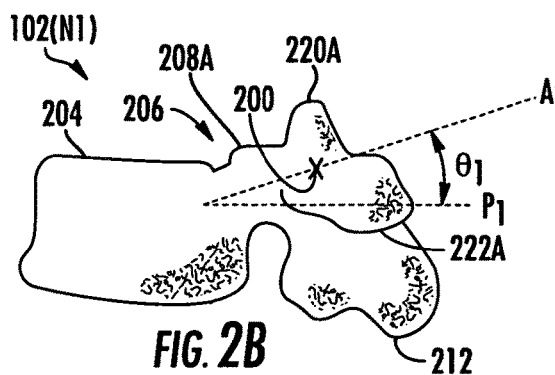
Figure 2C:
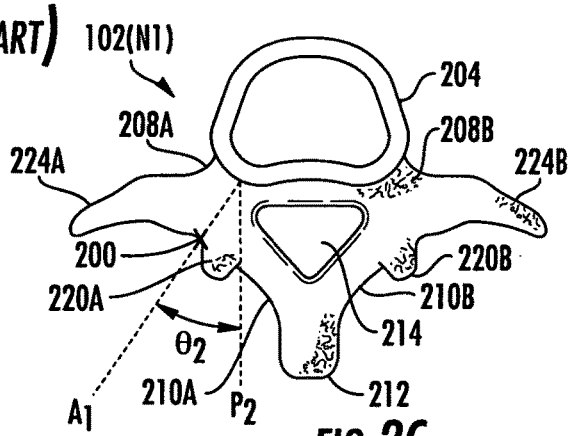

The desired trajectory A1 of the pedicle screw 108(N2) depends largely on the characteristic anatomy of the vertebra 102(N1). FIGS. 2A through 2C are a posterior close-up view, a left lateral view, and a superior view, respectively, of the vertebra 102(N1) of FIG. 1A illustrating as is known in the art an insertion point 200 of the respective pedicle screw 108(N2) of FIG. 1A without the respective pedicle screw 108(N2) inserted. Although the vertebrae 102(1)-102(N1) have different characteristics depending on their specific location as part of a spinal column 202 of the patient 104, generally each of the vertebra 102(1)-102(N1) includes a vertebral body 204 and a vertebral arch 206. The vertebral body 204 is arranged anteriorly and supports a weight of the patient 104 by serving as the structural foundation of the spinal column 202 and is separated from vertebral bodies 204 of adjacent vertebrae by intervertebral disks (not shown) which act as shock absorbers between adjacent ones of the vertebral bodies 204. The vertebral body 204 also supports the vertebral arch 206 of the vertebra 108(N2) comprising pedicles 208A, 208B and lamina 210A, 210B.

Figure 2D:
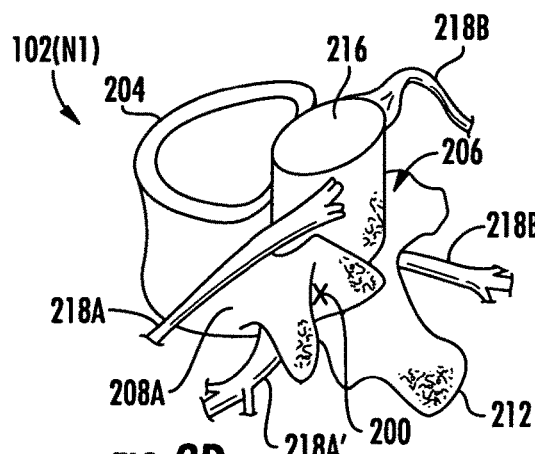
FIG. 2D is a superior perspective view of the vertebra of FIG. 2A illustrating the insertion point of FIG. 2A and spinal nerves of a spinal cord extending above and below the insertion point as is known in the art.

The desired trajectory A1 through the pedicle 208A is configured to avoid injury to the patient 104. The second pedicle 208B could also have a pedicle screw inserted therethrough, but for purposes of simplification and conciseness only the pedicle screw 108(N2) relative to the pedicle 208A is discussed herein. In this regard, FIG. 2D is a superior perspective view of the vertebra 102(N1) of FIG. 2A illustrating the insertion point 200 of FIG. 2A and spinal nerves 218A, 218A', 218B, 218B' extending from a spinal cord 216 as is known in the art. The pedicles 208A, 208B extend posteriorly and in divergent directions from the vertebral body 204 as two short stalk-like structures and are connected to the lamina 210A, 210B which extend further posteriorly and medially from the pedicles 208A, 208B to join together at the spinous process 212 to form the vertebral canal 214 (also known as the "vertebral foramen"). The vertebral canal 214 is the protected passageway within which the spinal cord 216 passes. The superior and inferior exterior surfaces of the pedicles 208A, 208B of adjacent ones of the vertebrae 102(1)-102(N1) form passageways for the spinal nerves 218A, 218A', 218B, 218B' to extend between these adjacent vertebrae and out from the spinal cord 216. The spinal nerves 218A, 218A' and the spinal cord 216 essentially surround in close proximity the pedicle 208A, and similarly the spinal nerves 218B, 218B' and the spinal cord 216 essentially surround in close proximity the pedicle 208B. For purposes of comparison the pedicle 208A may have a transverse diameter W1 in a range from four (4) to fifteen (15) millimeters. In contrast, the pedicle screw 108(N2) may have a diameter W2 in a second range from two (2) to twelve (12) millimeters and selected to be smaller than the transverse diameter W1 of the pedicle 108(N2). Accordingly, a relationship between the transverse diameter W1 of the pedicles 208A, 208B and the diameters W2 of the respective pedicle screws 108(N2) may be monitored, because breaches of the outside surface of the pedicles 208A, 208B into the spinal nerves 218A, 218A', 218B, 218B' and/or the spinal cord 216 may cause serious injury to the patient 104.

Figure 2E:
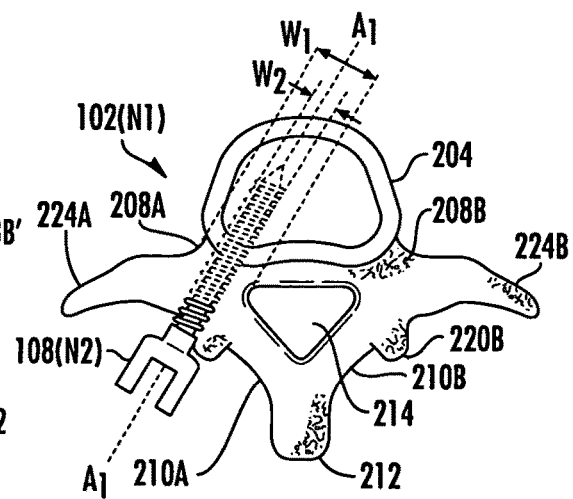
FIG. 2E is a superior view of the vertebra of FIG. 2A illustrated with the respective pedicle screw inserted therein by the pedicle screw system of FIG. 1B.

Further, features of the vertebral arch 206 enable the identification of the insertion point 200 of the trajectory A1 of the pedicle screw 108(N2). FIG. 2E is a superior view of the vertebra 102(N1) of FIG. 2A illustrated with the respective pedicle screw 108(N2) inserted therein by the pedicle screw system 116 of FIG. 1B. The vertebral arch 206 includes superior articulating processes 220A, 220B and inferior articulating processes 222A, 222B that project from the vertebral arch 206. These articulating processes 220A, 220B, 222A, 222B have cartilage-covered facets by which adjacent ones of the vertebrae 102(1)-102(N1) are joined. Also, at the juncture between the pedicles 208A, 208B and lamina 210A, 210B are transverse processes 224A, 224B that extend laterally and posteriorly. Ligaments and muscles are connected to the transverse processes 224A, 224B and the spinous process 212 to provide support and or articulation of the spinal column 202. These characteristics of the vertebra 102(N1) may be used to locate the insertion point 200 of the vertebra 102(N1) for the trajectory A1 of the pedicle screw 108(N2).

Knowing these characteristics of the vertebra 102(N1), the insertion point 200 of the desired trajectory A1 of the pedicle screw 108(N2) into the vertebra 102(N1) can be located, for example, relative to anatomical landmarks such as an intersection of a vertical line A2 through the superior articulating process 220A and the inferior articulating process 222A and a horizontal line A3 through the transverse processes 224A, 224B (FIG. 2A). Preoperative planning involving diagnostic tools (e.g., plain film radiography and computer-assisted tomography) may be utilized to assist in determining or confirming: the insertion point 200, bone quality, the pedicle transverse diameter W1 (FIG. 2E), a transverse pedicle angle θ1 relative to a transverse plane P1 (FIG. 2B), and a sagittal pedicle angle θ2 relative to a sagittal plane P2 (FIG. 2C). The transverse pedicle angle θ1 the sagittal pedicle angle θ2 may in combination with the insertion point 200 define the desired trajectory A1.

With reference back to FIG. 1B, the user 126 may use information gained from the preoperative planning to begin to insert the pedicle screw 108(N2) and rely on experience and tactile feedback ("feel") from the pedicle screw system 116 to determine whether the insertion of the pedicle screw 108(N2) appears to be progressing as expected along the desired trajectory A1 and whether the pedicle screw attachment 109(N2) with the vertebra 102(N1) appears to be strong and stable. If the pedicle screw attachment 109(N2) does not appear strong and stable, then there are several approaches that can be taken (e.g., increase the pedicle screw diameter W2 or change the desired trajectory A1). Specifically, the user 126 may reduce their workload that can unnecessarily lengthen a time to install the immobilization system 100 by using a power mode 400A of the multi-mode torque driver 118 when the confidence level is high that the desired trajectory A1 is correct and more extensive monitoring of tactile feedback is unnecessary. In cases when the user 126 has a lower confidence level of the correctness of the desired trajectory A1 or of the strength and stability of the pedicle screw attachment with the vertebra 102(N1), then the user 126 can insert the pedicle screw 108(N2) using a manual mode 400B of the multi-mode torque driver 118 to obtain tactile feedback at the expense of greater workload of the user 126. In this manner, the pedicle screw 108(N2) may be inserted into the vertebra 102(N1) while avoiding injury to the spinal cord 216 and the spinal nerves 218A, 218A' of the patient 104 as well as providing the efficiency and tactile feedback when needed to ensure the pedicle screw attachment 109(N2) is strong and stable.

Figure 3A:
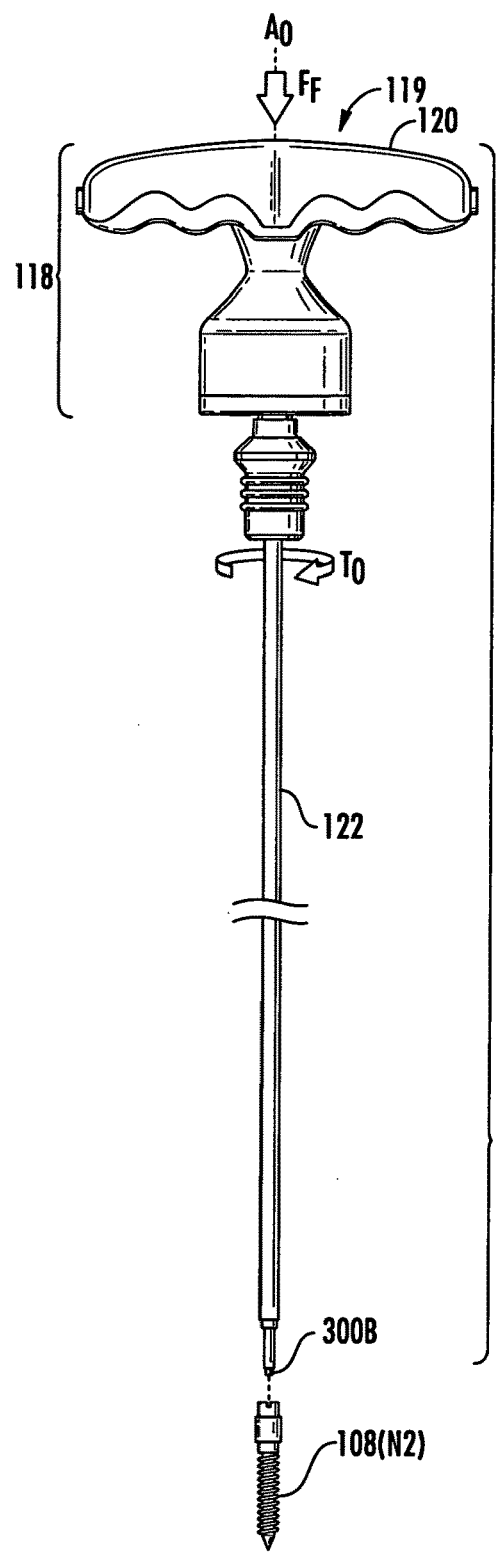
FIGS. 3A and 3B are a front view and a partially disassembled front view, respectively, of the exemplary pedicle screw system of FIG. 1B aligned along an output rotational axis with the pedicle screw.
Figure 3B:
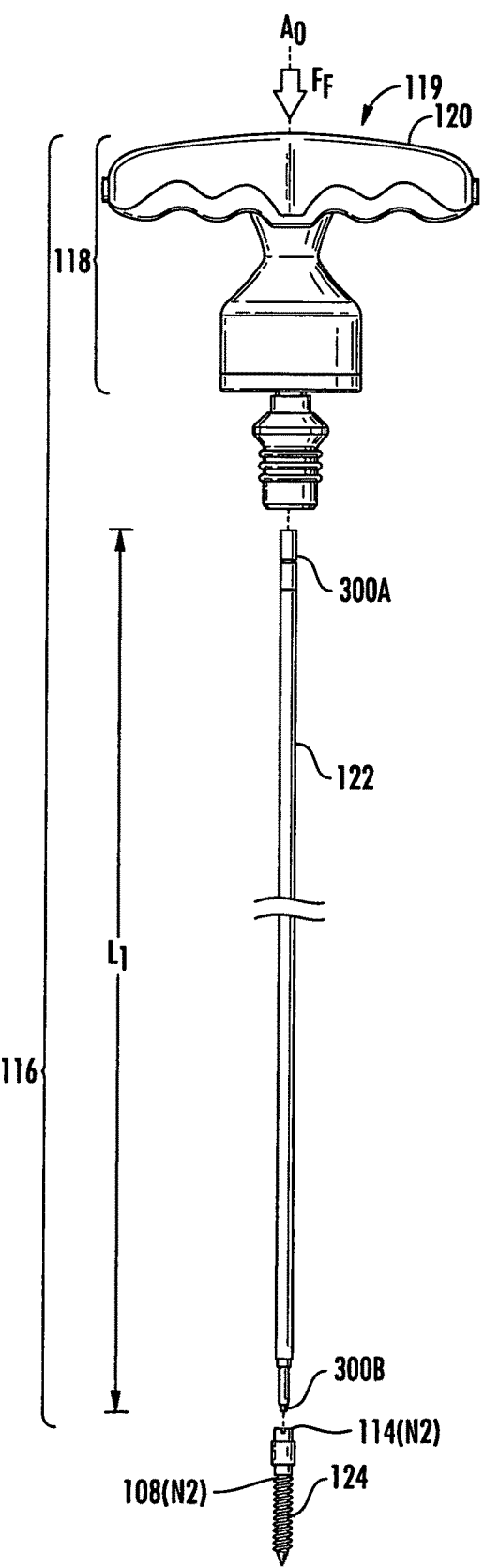

Now that the pedicle screw system 116 and the desired trajectory A1 of the pedicle screw 108(N2) have been introduced, details of the pedicle screw system 116 are now provided. FIGS. 3A and 3B are a front view and a partially disassembled front view, respectively, of the pedicle screw system 116 of FIG. 1B aligned with the pedicle screw 108(N2) along the output rotational axis A0. The pedicle screw system 116 includes the multi-mode torque driver 118, and the screw interface 122. Different types of the pedicle screw 108(N2) may be used according to the type of the immobilization system 100 (FIG. 1A) being created. Some of the pedicle screws 108(N2) present different interfaces for the pedicle screw system 116, so the screw interface 122 may be selected compatible with the pedicle screw 108(N2) and utilized as part of the pedicle screw system 116. The screw interface 122 extends longitudinally along the output rotational axis A0 and a length L1 from a standard connection end 300A to a screw coupling end 300B. The screw coupling end 300B is configured to couple with the pedicle screw 108(N2) and the standard connection end 300A is designed to couple with the adapter chuck 418, so that the system torque T0 may be transmitted between the multi-mode torque driver 118 and the screw interface 122 in at least one of a clockwise or counter-clockwise direction. In this manner, the multi-mode torque driver 118 may be used with different types of pedicle screws 108(1)-108(N2) by using different versions of the screw interface 122.

With continued reference to FIGS. 3A and 3B, the standard connection end 300A may have a standard coupling configuration (e.g., quarter inch square), so that the screw interface 122 may be compatible with coupling to various torque drivers, including the multi-mode torque driver 118. The screw interface 122 includes a length L1 which may be selected to allow the multi-mode torque driver 118 to be disposed the length L1 away from the vertebra 102(N1) during surgery to permit the user 126 to most conveniently perform other non-insertion tasks (e.g., wound drainage) around the vertebrae 102(1)-102(N1) without having the multi-mode torque driver 118 becoming an obstruction. Further, the screw interface 122 may be further selected based on the length L1 according to preference to experience a desirable degree of control of the transverse pedicle angle θ1 (FIG. 2B), and the sagittal pedicle angle θ2 (FIG. 2C)

during management of the pedicle screw attachments 109(1)-109(N2) with the vertebrae 102(1)-102(N1) along the desired trajectory A1, including insertion and retraction of the pedicle screws 108(1)-108(N2) relative to the vertebrae 102(1)-102(N1). Versions of the screw interface 122 with longer lengths L1 may have greater control of the transverse pedicle angle θ1 and the sagittal pedicle angle θ2. In this manner, the system torque T0 may be transmitted from the multi-mode torque driver 118 to the pedicle screws 108(1)-108(N2).

Figures 4A, 4B:
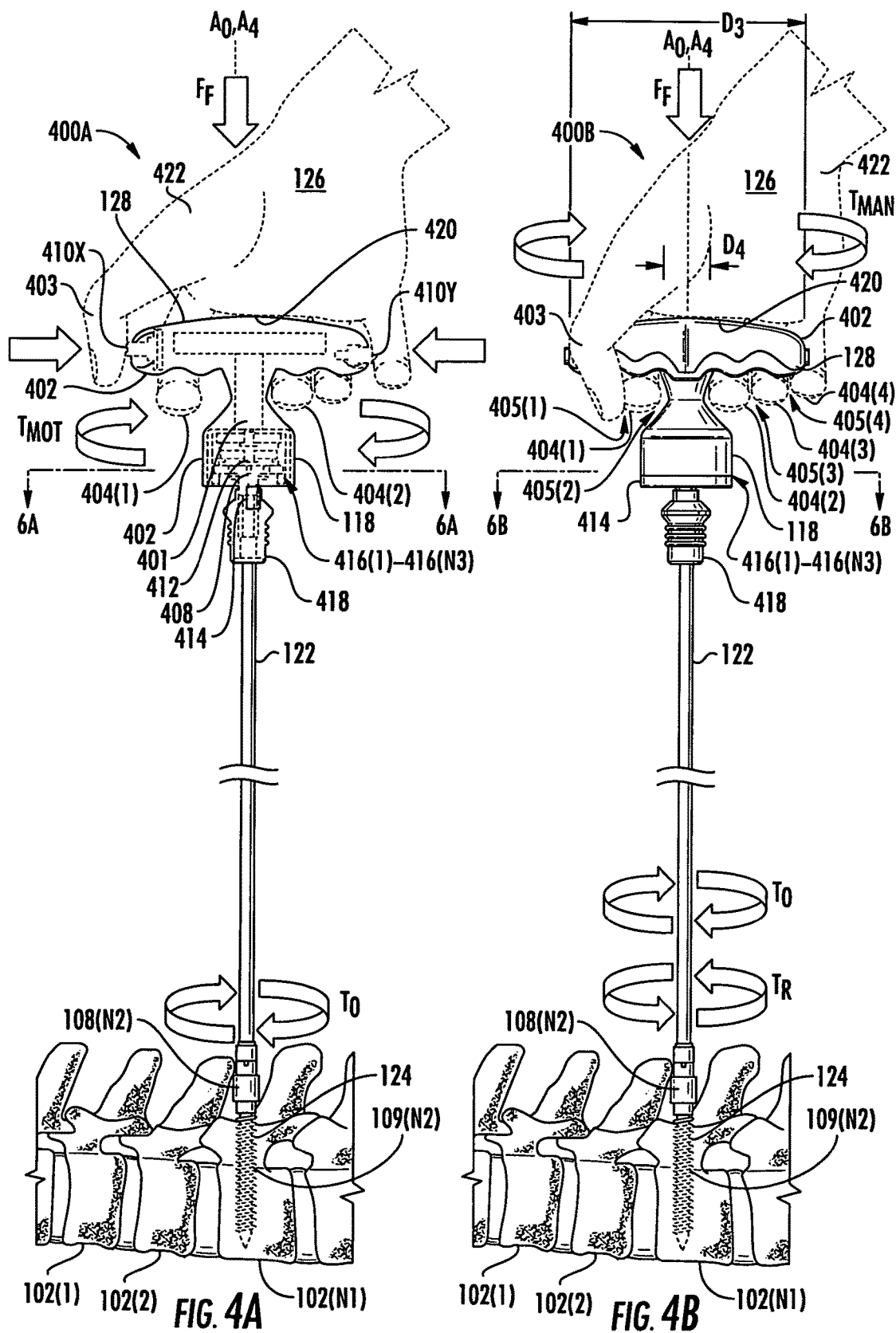
FIGS. 4A and 4B are side views of the multi-mode torque driver of FIG. 1B in a power mode and a manual mode, respectively, moving the pedicle screw relative to the vertebra to manage the pedicle screw attachment.
Figure 4C:
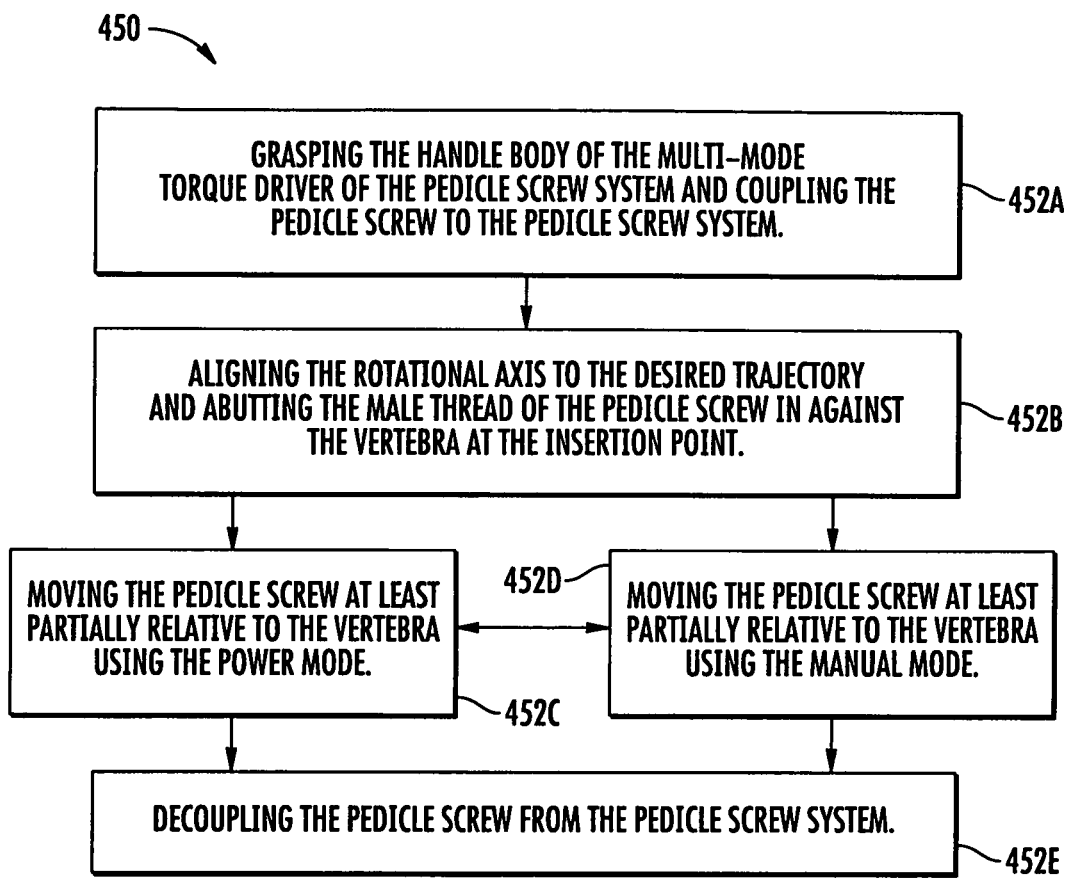
FIG. 4C is a flowchart of an exemplary method for managing the pedicle screw attachment with the vertebrae of FIG. 1B.

The multi-mode torque driver 118 of the pedicle screw system 116 transmits the system torque T0 to the pedicle screws 108(1)-108(N2) coupled thereto via the screw interface 122, so that the pedicle screw attachments 109(1)-109(N2) may be managed relative to the vertebrae 102(1)-102(N1). FIGS. 4A and 4B are side views of the multi-mode torque driver of FIG. 1B in a power mode 400A and a manual mode 400B, respectively, moving the pedicle screws 108(1)-108(N2) relative to the vertebrae 102(1)-102(N1) to manage the pedicle screw attachment. Further, FIG. 4C is a flowchart of an exemplary method 450 for managing the pedicle screw attachment with the vertebrae 102(1)-102(N1) of FIG. 1B. The method 450 is now discussed using the terminology discussed above and below in relation to the operations 452A through 452E as depicted in FIG. 4C. In this manner, the user 126 may conveniently select combinations of the power mode 400A and the manual mode 400B of the multi-mode torque driver 118 during the insertion or retraction of the pedicle screw 108(N2).

In order to prepare the pedicle screw system 116 for either the power mode 400A or the manual mode 400B, the user 126 may grasp the handle body 119 of the multi-mode torque driver 118 and couples the pedicle screw 108(N2) to the pedicle screw system 116 (operation 452A of FIG. 4C). For the embodiment of the handle body 119 as the T-shaped body 120, the user 126 may grasp the gripper handle portion 128 with the output rotational axis A0 of the multi-mode torque driver 118 disposed within interdigital spaces 405(2)-405(4) between adjacent ones of the fingers 404(1)-404(4) of the user 126. In this manner, the user 126 establishes an ergonomic coupling with the multi-mode torque driver 118 that enables a high degree of control of the pedicle screw system 116 and facilitates a high degree of tactile feedback for precise monitoring of the pedicle screw attachment when a manual mode 400B is selected by the user 126.

While grasping the handle body 119, the method 450 may also include the user 126 abutting the male thread 124 of the pedicle screw 108(N2) against the vertebra 102(N1) and aligning the longitudinal axis A4 the pedicle screw 108(N2) and the output rotational axis A0 of the pedicle screw system 116 with the desired trajectory A1 while the pedicle screw 108(N2) is coupled with the pedicle screw system 116 (operation 452B of FIG. 4C). In this manner, the pedicle screw system 116 may be prepared to enter either the power mode 400A or the manual mode 400B.

Upon the user 126 selecting the power mode 400A to gain high efficiency at the expense of lower tactile feedback, the method 450 further includes at least partially moving the pedicle screw 108(N2) relative to the vertebra 102(N1) by applying the system torque T0 to the pedicle screw 108(N2) in the power mode 400A (operation 452C of FIG. 4C). The user 126 may enter the power mode 400A by generating, with a motor assembly 401 disposed in the handle body 119, a motorized torque $T_{MOT}$ and applying the motorized torque $T_{MOT}$ to the anti-backdrive unit 408 of the multi-mode torque driver 118. The motor assembly 401 may generate the motorized torque $T_{MOT}$ when at least one switch 410X, 410Y of the multi-mode torque driver 118 is activated by the user 126. The system torque T0 includes the motorized torque $T_{MOT}$ in the power mode 400A. Then at least one switch 410X, 410Y may be conveniently disposed within the handle body 119 to facilitate one-hand operation by the user 126. In the embodiment of the handle body 119 as the T-shaped body 120, then the at least one switch 410X, 410Y may be disposed in the gripper handle portion 128 for convenient one-hand operation. Once generated, the motorized torque $T_{MOT}$ becomes available to the anti-backdrive unit 408 at an output interface 412 of the motor assembly 401. In this manner, the power mode 400A is initiated by generating the motorized torque $T_{MOT}$.

Moreover, during the power mode 400A, the pedicle screw 108(N2) receives the motorized torque $T_{MOT}$ as the system torque T0 of the multi-mode torque driver 118. In this regard, the output interface 412 of the motor assembly 401 engages with and transfers the motorized torque $T_{MOT}$ to the output element 414 of the anti-backdrive unit 408 without mechanical interference from at least one locking element 416(1)-416(N3) of the anti-backdrive unit 408. In the absence of this mechanical interference, the motorized torque $T_{MOT}$ is transferred to the output element 414 that is, in turn, coupled to the adapter chuck 418. As the adapter chuck 418 is rotationally coupled to the pedicle screw 108(N2) through the screw interface 122, the pedicle screw 108(N2) receives the motorized torque $T_{MOT}$ as the system torque T0 that causes the pedicle screw 108(N2) to rotate. As the male thread 124 of the pedicle screw 108(N2) abuts against the vertebra 102(N1), the pedicle screw 108(N2) is inserted into (or retracted from) the vertebra 102(N1) as the pedicle screw 108(N2) rotates in response to the system torque T0 applied. In this manner, the pedicle screw attachment 109(N2) with the vertebra 102(N1) may be managed by inserting or retracting the pedicle screw 108(N2) using the power mode 400A.

It is noted that the efficiency of the movement of the pedicle screw 108(N2) may be further facilitated for the embodiment of the handle body 119 as the T-shaped body 120 by applying the feed force $F_F$ with a palm 420 of a hand 422 of the user 126. In this embodiment of the handle body 119, the palm 420 may be disposed during application of feed force $F_F$ with the output rotational axis A0 intersecting the palm 420. The feed force $F_F$ may be applied in the power mode 400A or the manual mode 400B. In this manner, the feed force $F_F$ may be applied co-linearly with the rotational axis A0 for accuracy and efficiency of the movement of the pedicle screw 108(N2).

In contrast to the efficiency provided by the power mode 400A, the user 126 may select the manual mode 400B based on several factors. For example, when confirming the strength and long-term stability of the pedicle screw attachment 109(N2) with the vertebra 102(N1), the user 126 may select the manual mode 400B. The manual mode 400B involves the application of the manual torque $T_{MAN}$ to the handle body 119 by the user 126 as the user 126 monitors changes in the resistance torque $T_R$ which opposes the manual torque $T_{MAN}$. The resistance torque $T_R$ is a measure of the strength and stability of the pedicle screw attachment $T_R$ that is, as discussed above, formed by at least one of friction and mechanical interference between the pedicle screw 108(N2) and the vertebrae 102(N1) and can be more easily perceived by the user 126 as tactile feedback during the manual mode 400B, than occurring in response to the motorized torque $T_{MOT}$ during the power mode 400A. A higher value of the resistance torque $T_R$ is generally associated with a stronger and more stable quality of the pedicle screw attachment 109(N2). Accordingly, when the user 126 has high confidence in the pedicle screw attachment 109 (N2), then the user 126 may select the power mode 400A for efficient movement of the pedicle screw 108(N2) relative to the vertebra 102(N1). In this manner, the user 126 may alternate between the power mode 400A and the manual mode 400B to achieve pedicle screw attachments that are more efficiently managed while avoiding high failure rates of the pedicle screw attachment 109(N2).

With reference back to FIG. 4B, the method 450 also includes at least partially moving the pedicle screw 108(N2) relative to the vertebra 102(N1) by applying the system torque T0 to the pedicle screw 108(N2) in the manual mode 400B (operation 452D of FIG. 4C). Specifically, the user may enter the manual mode 400B by applying the manual torque $T_{MAN}$ to the handle body 119 when the pedicle screw 108(N2) is coupled with the pedicle screw system 116 and the anti-backdrive unit is free of the motorized torque $T_{MAN}$ from the motor assembly 401. In response to a resistance to rotation offered by the pedicle screw 108(N2) coupled to the pedicle screw system 116 and held initially in place by an abutment against the vertebra 102(N1), the output element 414 of the anti-backdrive unit 408 initially rotates relative to the output interface 412 of the motor assembly 401. Initial rotation is possible, because the output element 414 is free of the motorized torque $T_{MOT}$. This initial rotation causes the locking elements 416(1)-416(N) to lock the output interface 412 of the motor assembly 401 relative to the handle body 119, which then stops the initial rotation of the output element 414 relative to the handle body 119 and facilitates the manual torque $T_{MAN}$ to be transmitted through the adapter chuck 418 as the system torque T0 for the pedicle screw 108(N2) via the output element 414. Accordingly, as the male thread 124 of the pedicle screw 108(N2) abuts against the vertebra 102(N1), the pedicle screw 108(N2) is inserted into or retracted from the vertebra 102(N1) as the pedicle screw 108(N2) rotates in response to the system torque T0 applied. In this manner, the pedicle screw 108(N2) may be inserted (or retracted) using the manual mode 400B.

Figures 1, 4D:
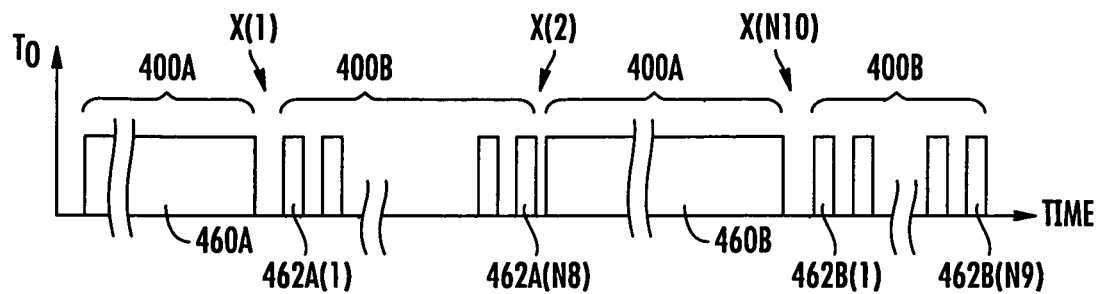
FIGS. 4D-1 and 4D-2 are exemplary graphs of system torque produced by the multi-mode torque driver of FIG. 4A and resistance torque provided to the multi-mode torque driver, respectively, over an exemplary time period during the power and manual modes illustrating the resistance torque above a resistance threshold.
Figures 2, 4D:
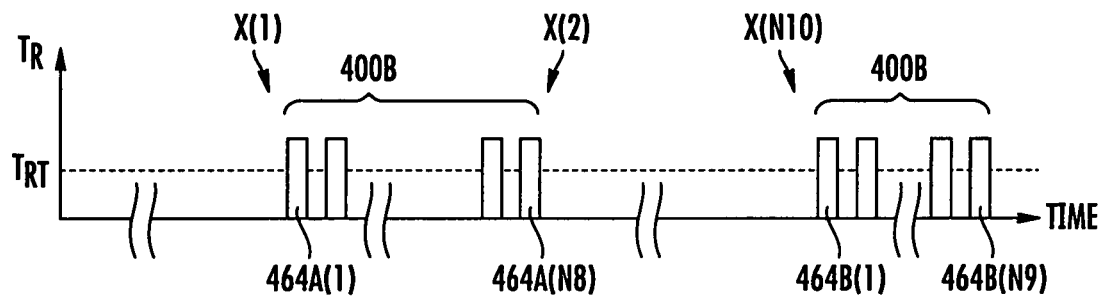

The multi-mode torque driver 118 is configured to facilitate decisions regarding transitions between the power mode 400A and the manual mode 400B. In this regard, FIGS. 4D-1 and 4D-2 are exemplary graphs of the system torque T0 produced by the multi-mode torque driver 118 of FIG. 4A and the resistance torque $T_R$ provided to the multi-mode torque driver 118, respectively, over an exemplary time period during the power mode 400A and the manual mode 400B. FIG. 4D-1 illustrates at least one power instance 460A, 460B of the power mode 400A producing the system torque T0, including the motorized torque $T_{MOT}$. The system torque T0 is illustrated as constant during each of the power modes 400A, but in other embodiments of the multi-mode torque driver 118 the system torque T0 may be variable. Also, during the time period, the system T0 may include manual applications 462A(1)-462A(N8) of the manual torque $T_{MAN}$ that are applied by the user 126 between the power instances 460A, 460B, and manual applications 462B (1)-462B(N9) of the manual torque $T_{MAN}$ subsequent to the power instance 460B. Each of the manual applications 462A(1)-462A(N8), 462B(1)-462B(N9) represent sequential applications of the manual torque $T_{MAN}$ applied to the pedicle screw 108(N2) as the pedicle screw 108(N2) is rotated during pedicle screw attachment management. The user 126 performs transitions X(1)-X(N10) between the power mode 400A and the manual mode 400B based on efficiency and the quality of the pedicle screw attachment 109(N2). The quality (e.g., strength and stability) of the pedicle screw attachment 109(N2) may be at least partially measured as the resistance torque $T_R$ available to be perceived by the user 126 through the handle body 119 during the manual mode 400B. FIG. 4D-2 illustrates the resistance torque $T_R$ generated during the manual mode 400B illustrated in FIG. 4D-1. The observations 464A(1)-464A(N8) of the resistance torque $T_R$ generated immediately subsequent to the transition X(1) exceeds a resistance torque threshold $T_{RT}$ and this may result in a higher confidence that the pedicle screw attachment 109(N2) is strong and stable. The user 126 may subjectively establish the resistance torque threshold $T_{RT}$ based on experience and may be a qualitative or quantitative value, for example, one (1) Newton-meter. Accordingly, the user 126 may initiate the transition X(2) from manual mode 400B to power mode 400A based on observations 464A(1)-464A(N8) of the resistance torque $T_R$ received immediately subsequent to the transition X(1).

Moreover, the user 126 may continue with the power mode 400A during the power instance 460B as long as there is confidence that there is a strong and stable attachment. As shown in FIG. 4D-1, the transition X(N10) from the power mode 400A to the manual mode 400B may be initiated by the user 126 to assist in determining whether the pedicle screw attachment 109(N2) with the vertebra 102(N1) remains strong and stable. As is depicted in the associated FIG. 4D-2, observations 464B(1)-464B(N9) of the resistance torque $T_R$ generated immediately after the transition X(N10) exceeds the threshold torque $T_{RT}$ and this may indicate that the pedicle screw attachment 109(N2) is strong and stable. The user 126 may engage in various combinations of the transitions X(1)-X(N10) to ensure high confidence that a strong and stable quality of the pedicle screw attachment 109(N2) has been achieved.

Figures 1, 4E:
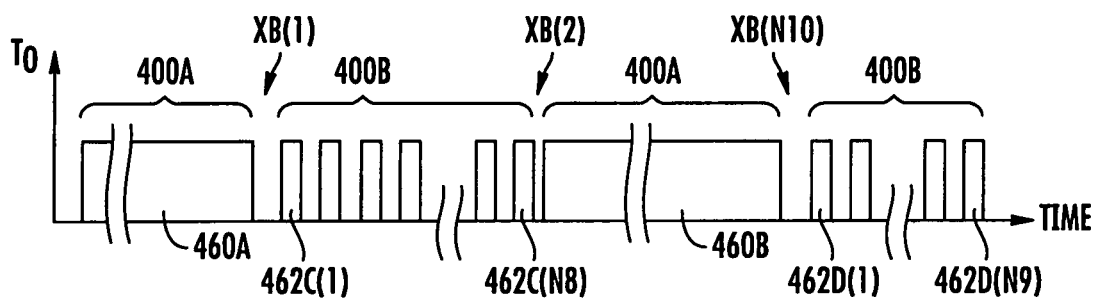
Figures 2, 4E:
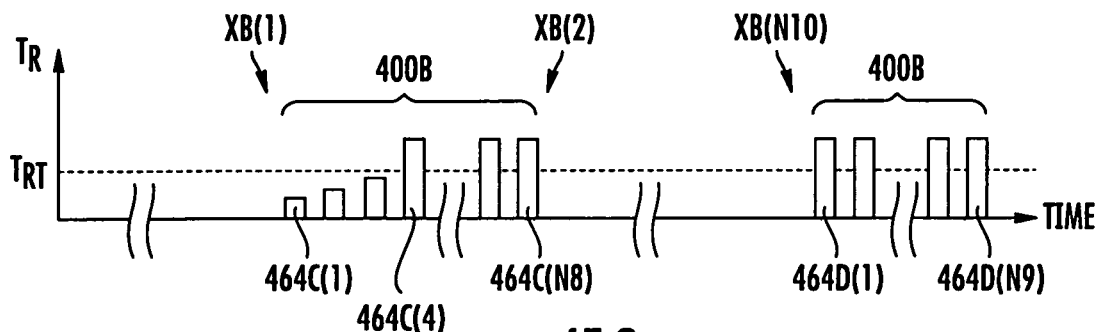

In contrast, FIGS. 4E-1 and 4E-2 are exemplary graphs of system torque T0 produced by the multi-mode torque driver of FIG. 4A and resistance torque $T_R$ provided to the multi-mode torque driver 118, respectively, over an exemplary second time period during the power mode 400A and the manual mode 400B illustrating the resistance torque $T_R$ temporarily below the resistance threshold $T_{RT}$. During this second time period, the user 126 initiates a transition XB(1) from the power mode 400A to the manual mode 400B, a transition XB(2) from the manual mode 400B to the power mode 400A, and a transition XB(N10) from the power mode 400A to the manual mode 400B. The manual applications 462C(1)-462C(N8), 462D(1)-462D(N9) of the system torque T0 in the manual mode 400B may respectively result in the resistance torque $T_R$ as represented by the observations 464C(1)-464C(N8), 464D(1)-464D(N9). The observations 464C(1)-464C(3) are below the resistance torque threshold $T_{RT}$. Upon receiving the observations 464C(1)-464C(3), the user 126 may decide that the confidence level in the strength and stability of the pedicle screw attachment 109(N2) is not high. In response, the user 126 may delay the transition XB(2) to the power mode 400A and thereby receive additional observations 464C(4)-464C(N8) to determine whether the confidence level may have increased or take other responsive actions (e.g., use thicker pedicle screw and/or change desired trajectory A1). In this exemplary situation exhibited in FIG. 4E-2, the additional observations 464C(4)-464C(N8) exceed the resistance torque threshold $T_{RT}$, and so the confidence level may be increased where the user 126 initiated the transition XB(2) from the manual mode 400B to the power mode 400A. The observations 464C(4)-464C(N8) also exceeded the resistance torque threshold $T_{RT}$ and these observations 464C(4)-464C(N8) may indicate that the pedicle screw attachment 109(N2) is strong and stable.

In summary, automatic transitions between the power mode 400A and the manual mode 400B are made possible with the anti-backdrive unit 408 when the pedicle screw 108(N2) is coupled with the pedicle screw system 116. The automatic transition to the power mode 400A is initiated by transmitting the motorized torque $T_{MOT}$ from the motor assembly 401 to the anti-backdrive unit 408. Alternatively, the automatic transition to the manual mode 400B may be initiated by the user 126 by applying the manual torque $T_{MAN}$ to the handle body 119 while the pedicle screw 108(N2) is coupled to the output element 414 of the anti-backdrive unit 408 and the pedicle screw 108(N2) is receiving rotational resistance from the vertebra 102(N1) in the absence of the motorized torque $T_{MOT}$. The automatic transitions expedite the surgical process and promote surgical accuracy as the user 126 may use the power mode 400A for efficiency yet conveniently transition, when desired, to and from the manual mode 400B to confirm the pedicle screw attachment 109(N2) to the vertebra 102(N1) is strong and stable. The automatic transitions also minimize a quantity of switches needed for the user 126 to control the multi-mode torque driver 118.

The method 450 also includes decoupling the pedicle screw 108(N2) from the pedicle screw system 116 once the pedicle screw attachment has been achieved (Operation 452E of FIG. 4C). The pedicle screw 108(N2) may be disengaged from the screw interface 122 of the pedicle screw system 116 once the movement of the pedicle screw 102(N1) is no longer necessary for the pedicle screw attachment 109(N2). In this manner, the pedicle screw attachment 109(N2) may be completed, so that the immobilization rod 106 may be later fastened to the pedicle screw 108(N2) to form the immobilization system 100 (FIG. 1A).

Now that the method 450 of the pedicle screw system 116 has been introduced, details of the components of the multi-mode torque driver 118 are now provided. FIGS. 5A through 5G are a top perspective view, front view, right side view, partial front view, top view, bottom view, and exploded view, respectively, of the multi-mode torque driver 118 of the pedicle screw system 116 of FIG. 1B. The multi-mode torque driver 118 may include the motor assembly 401, anti-backdrive unit 408, a battery 500, handle body 119, adapter chuck 418, and switches 410X, 410Y. Each of these will now be discussed sequentially in detail.

The motor assembly 401 provides motor rotational energy, including the motorized torque $T_{MOT}$ during the power mode 400A. The rotational energy includes a motorized torque $T_{MOT}$ in a range from two (2) Newton-meters to ten (10) Newton-meters and a rotational speed in a second range from fifty (50) RPM to two hundred (200) RPM. The motorized torque $T_{MOT}$ is provided to be sufficient to move the pedicle screw 108(N2) along the desired trajectory A1 as the male thread 124 of the pedicle screw 108(N2) abuts against the vertebrae 102(N1). The rotation speed is configured to insert the pedicle screw 108(N2) into the vertebrae 102(N1) in less than thirty (30) seconds and preferably approximately fifteen (15) seconds when the pedicle screw requires less than thirty (30) rotations to form the pedicle screw attachment 109(N2). It is noted that establishing the pedicle screw attachment 109(N2) may involve other ancillary tasks (e.g., tapping and verifying the desired trajectory A1) that may take up additional time that may not be represented in the less than thirty (30) seconds.

Moreover, the motor assembly 401 may include an electric motor 502 coupled to a drive train 504 to collectively produce the motorized torque $T_{MOT}$ and the rotational speed. The electric motor 502 may, for example, be a direct current (DC) electric motor. The electric motor 502 may be supplied power from the battery 500. The electric motor 502 may support both clockwise and counterclockwise generation of rotational energy that may be transmitted as the motorized torque $T_{MOT}$. In this manner, the motorized torque $T_{MOT}$ may be generated during the power mode 400A.

It is envisioned that in future alternative embodiments the electric motor 502 may supply the motorized torque $T_{MOT}$ and rotational speed without the drive train 504. However, in the embodiments illustrated herein the drive train 504 of the motor assembly 401 may include epicyclic gearing including, for example, first and second planetary gear stages 506A, 506B (FIG. 5G) to provide the high torque and appropriate rotational speed consistent with managing the pedicle screw attachment 109(N2). The first planetary gear stage 506A may be linked to the electric motor 502 with a sun gear 508. The first planetary gear stage 506A may include a plurality of first planet gears 510A(1)-510A(N4) in communication with annulus gear teeth 512 of an intermediate sleeve 513 of the handle body 119 and supported by a carrier backplane 514. An output sun gear 516 of the first planetary gear stage 506A may be input into a second planetary gear stage 506B. The second planetary gear stage 506B may include a plurality of second planet gears 510B(1)-510B(N5) in communication with the annulus gear teeth 512 of the handle body 119 and supported by the output interface 412 of the motor assembly 401. Each of the first and second planetary gear stages 506A, 506B may have a ratio in a range from 1:9 to 1:13, and preferably 1:11. The first and second planetary gear stages 506A, 506B may be made of a strong rigid material, for example, a metal or plastic (e.g., polyetherimide provided by SABIC of Pittsfield, Mass.). In this manner, the motorized torque $T_{MOT}$ may be provided to the anti-backdrive unit 408 by the output interface 412 of the motor assembly 401 during the power mode 400A.

With continued reference to FIGS. 5A through 5G, the anti-backdrive unit 408 enables the system torque T0 to be transmitted to the pedicle screw 108(N2), wherein the system torque T0 includes the motorized torque $T_{MOT}$ in the power mode 400A and the $T_{MAN}$ in the manual mode 400B. The anti-backdrive unit 408 includes the output element 414, the locking elements 416(1)-416(N3), collar portion 524, and the housing portion 520. These components of the anti-backdrive unit 408 function cooperatively with the handle body 119 and the output interface 412 of the motor assembly 401 to facilitate the transition between the power mode 400A and the manual mode 400B. Specifically, the output element 414 of the anti-backdrive unit 408 includes radial elements 517(1)-517(N6) and the output interface 412 of the motor assembly 401 includes post portions 518(1)-518(N7) which may rotate concentrically with the locking elements 416(1)-416(N3) around the output rotational axis A0 and within an inner circumferential surface 522 of a housing portion 520. The housing portion 520 and the collar portion 524 may be statically coupled to the handle body 119. The housing portion 520 and the output element 414 in combination with the collar portion 524 and the output interface 412 may form at least one enclosure to contain the locking elements 416(1)-416(N3). The position of the locking elements 416(1)-416(N3) relative to the radial elements 517(1)-517(N6) and the post portions 518(1)-518(N7) determines whether the multi-mode torque driver 118 operates in the power mode 400A or the manual mode 400B.

Details of the anti-backdrive unit 408 are now discussed. In this regard, FIGS. 6A and 6B that are partial top sectional views parallel to the output rotational axis A0 of the multi-mode torque driver 118 in FIGS. 4A and 4B, respectively, illustrating the anti-backdrive unit 408 operating in the power mode 400A and the manual mode 400B. As shown in the exemplary power mode 400A illustrated in FIG. 6A, the post portions 518(1)-518(N7) of the output interface 412 of the motor assembly 401 may be rotated about the output rotational axis A0 by the motorized torque $T_{MOT}$. The post portions 518(1)-518(N7) abut against and urge the locking elements 416(1), 416(3), 416(5) to rotate about the output rotational axis A0 in the same direction while being guided along a circumferential path by the inner circumferential surface 522. In response to being urged, the locking elements 416(1), 416(3), 416(5) abut against the radial elements 517(1)-517(N6) of the output element 414 of the anti-backdrive unit 408 to transmit the motorized torque $T_{MOT}$ to the pedicle screw 108(N2) as the system torque T0 through the output element 414. Also, the locking elements 416(2), 416(4), 416(N3) do not offer significant resistance to the transfer of this rotational energy of the motorized torque $T_{MOT}$, because the radial elements 517(1)-517(N6) abut against and urge the locking elements 416(2), 416(4), 416(N3) to rotate about the output rotational axis A0 in the same direction and rotational speed as the locking elements 416(1), 416(3), 416(5). In this manner, the anti-backdrive unit 408 transfers the motorized torque $T_{MOT}$ to the pedicle screw 108(N2) as the system torque T0 via the anti-backdrive unit 408.

The power mode 400A enables the motorized torque $T_{MOT}$ to be transferred to the output element 414 without the locking elements 416(1)-416(N3) locking the output element 414 relative to the inner circumferential surface 522 that is statically coupled to the handle body 119. In the exemplary output element 414 of FIG. 6A the radial elements 517(1)-517(N6) are connected by an external surface 528. This external surface 528 is arranged to be non-concentric with the inner circumferential surface 522 when rotating about the output rotational axis A0. Accordingly, locking may be avoided by maintaining the locking elements 416(1)-416(N3) in positions where the localized separations between the inner circumferential surface 522 and the external surface 528 are greater than the respective widths D0 of the locking elements 416(1)-416(N3) at those positions. By virtue of the non-concentricity, it is noted that nearest the radial elements 517(1)-517(N6) the localized separation is a distance D1 and increases to a local separation of distance D2 at positions further from the radial elements 517(1)-517(N6). As is shown in the power mode 400A illustrated in FIG. 6A, locking is avoided because the locking elements 416(1)-416(N3) are maintained in positions against the radial elements 517(1)-517(N6) where the localized separations between the inner circumferential surface 522 and the external surface 528 are greater than the respective widths D0 of the locking elements 416(1)-416(N3). In this manner, the motorized torque $T_{MOT}$ is most efficiently transmitted as the system torque T0 through the anti-backdrive unit 408 in the power mode 400A.

In contrast, in the exemplary manual mode 400B illustrated in FIG. 6B, the output element 414 of the anti-backdrive unit 408 receives the manual torque $T_{MAN}$ and rotates about the output rotational axis A0. As the motor assembly 401 remains inactive (free of motorized torque $T_{MOT}$) during the manual mode 400B, the post portions 518(1)-518(N7) are urged to move circumferentially about the output rotational axis A0 as the radial elements 517(1)-517(N6) abut against the post portions 518(1)-518(N7) through the locking elements 416(2), 416(4), 416(N3). The locking elements 416(1), 416(3), 416(5) establish a lock preventing the output element 414 from moving relative to the inner circumferential surface 522 which is static relative to the handle body 119, because the housing portion 520 is statically coupled to the handle body 119 via the intermediate sleeve 513. This locking in the form of mechanical interference occurs, because the post portions 518(1)-518(N7) are not purposely sized circumferentially long enough to displace these locking elements 416(1), 416(3), 416(5) to positions where the localized separations between the inner circumferential surface 522 and the external surface 528 are greater than the respective widths D0. Instead, locking results, because the locking elements 416(1), 416(3), 416(5) are disposed in positions where the localized separation distance of D2 is no more than the widths D0 of the locking elements 416(1), 416(3), 416(5). In this manner, the locking achieved in the anti-backdrive unit 408 couples the output element 414 of the anti-backdrive unit 408 to the inner circumferential surface 522 of the housing portion 520 which statically coupled to the handle body 119 during the manual mode 400B and this locking enables the manual torque $T_{MAN}$ applied by the user 126 at the gripper handle portion 128 of the handle body 119 to be transmitted to the pedicle screw 108(N2) through the anti-backdrive unit 408.

It is noted that the locking elements 416(1)-416(N3) may include either a spherical shape or cylindrical shape to easily engage and disengage with the radial elements 517(1)-517(N6) and the post portions 518(1)-518(N7). The spherical shape or cylindrical shape also enables the locking elements 416(1)-416(N3) to efficiently move circumferentially about the output rotational axis A0 along the inner circumferential surface 522 of the housing portion 520. In this manner, the locking elements 416(1)-416(N3) enable more efficient transitions between the power mode 400A and the manual mode 400B.

Next, with reference back to FIGS. 5A through 5G, the battery 500 provides energy to the motor assembly 401 during the power mode 400A. The battery 500 provides electrical energy to be converted by the electric motor 502 to the motorized torque $T_{MOT}$. The battery 500 may be, for example, a lithium-ion polymer battery having a voltage, for example, in a range from three (3) to ten (10) volts. The battery 500 may include connectivity elements 530A, 530B (see FIG. 5D) having electrically conductive materials to transfer energy of the battery 500 to the electric motor 502. In this manner, the battery 500 may facilitate the generation of the motorized torque $T_{MOT}$ at the electric motor 502.

Figure 7E:
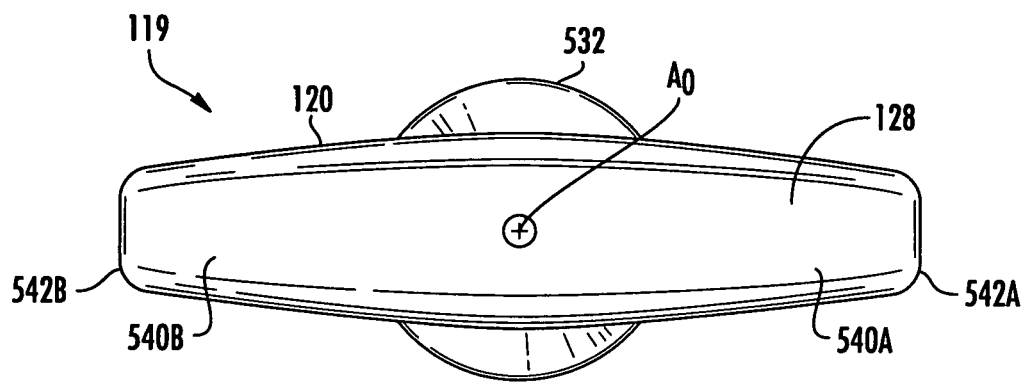
Figure 7F:
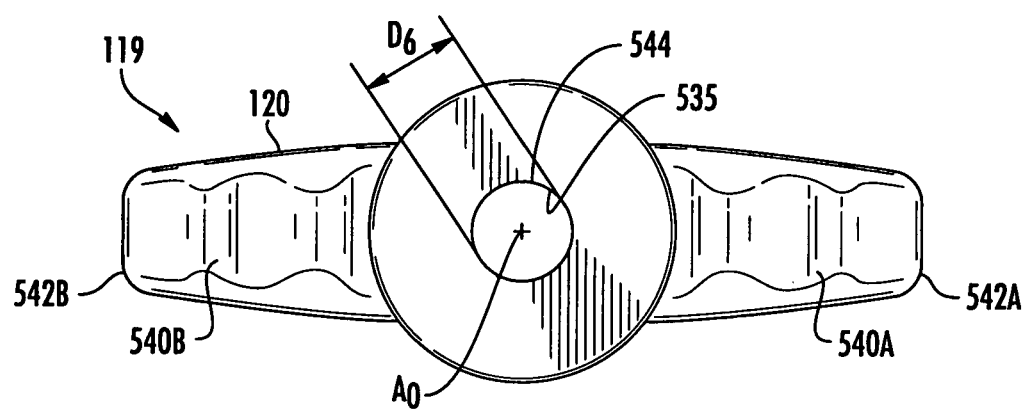
Figure 8G:
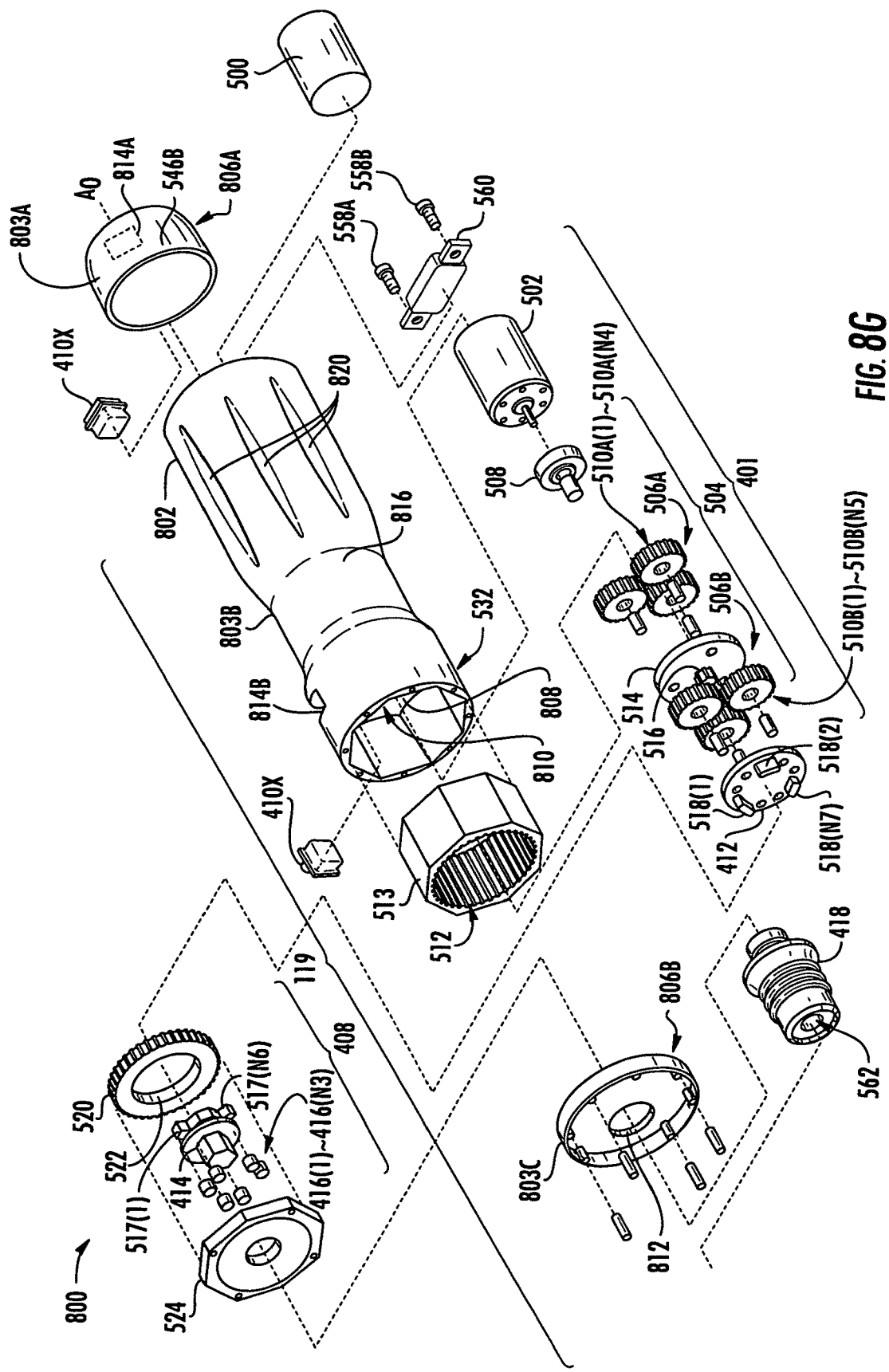
Figure 9A:
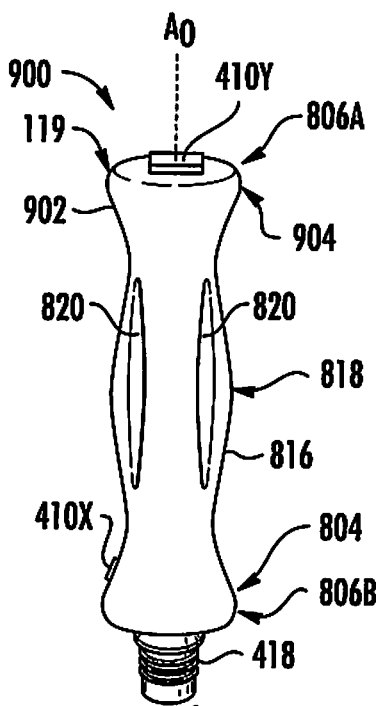
FIGS. 9A through 9E are a top perspective view, front view, left side view, top view, and bottom view, respectively, of a third exemplary embodiment of a multi-mode torque driver compatible with the screw interface of FIG. 1B, wherein a handle body in this second embodiment is a second axially-shaped body with a second flared end.
Figure 9B:
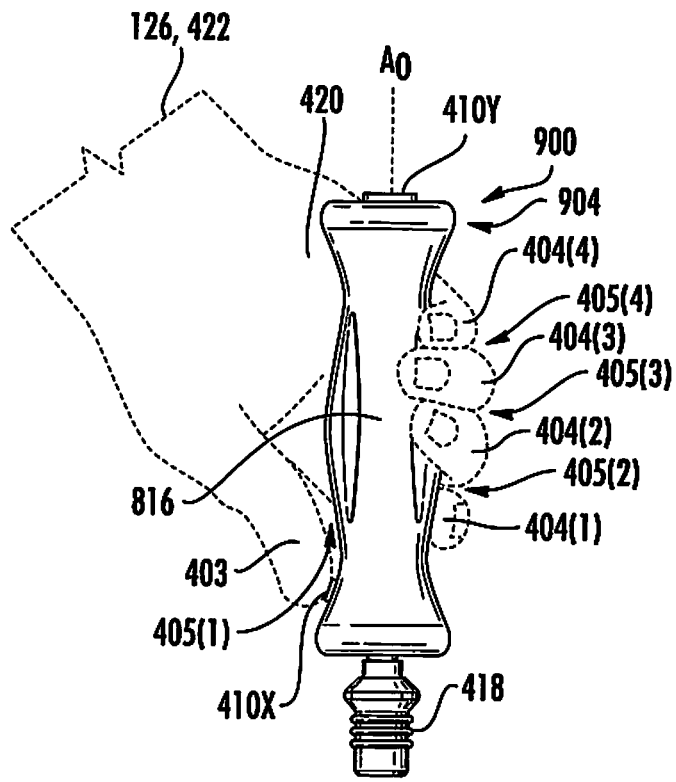
Figure 9C:
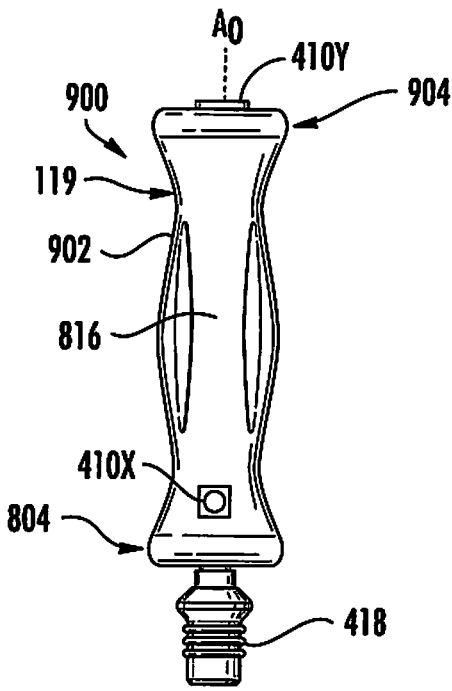
Figure 9D:
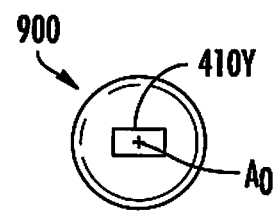
Figure 9E:
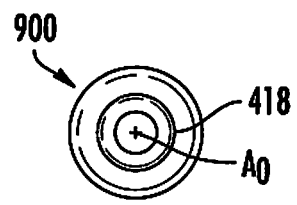
Figure 10A:
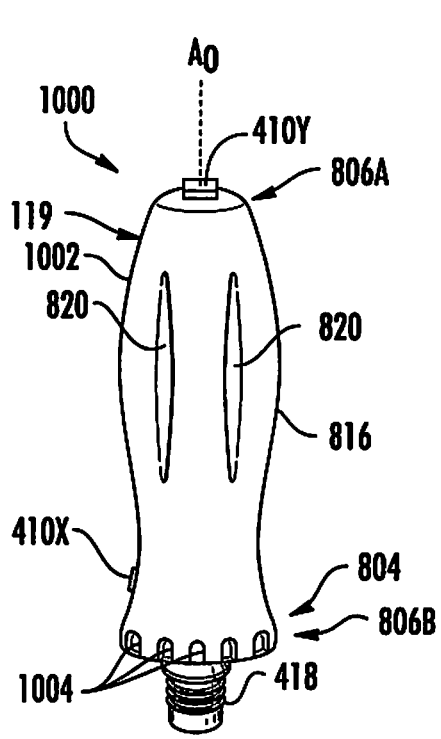
FIGS. 10A through 10E are a top perspective view, front view, left side view, top view, and bottom view, respectively, of a fourth exemplary embodiment of a multi-mode torque driver compatible with the screw interface of FIG. 1B, wherein a handle body in this fourth embodiment is an axially-shaped body with flared end grooves.
Figure 10B:
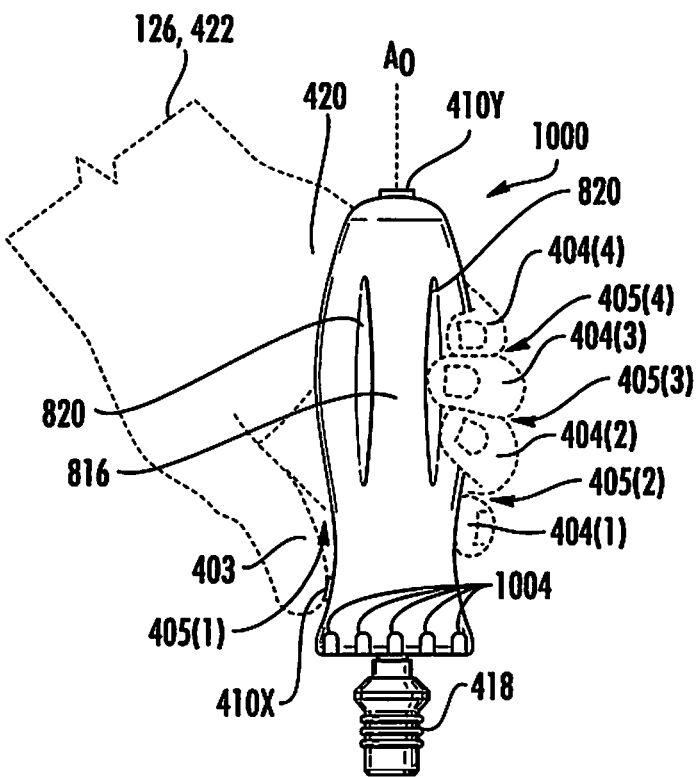
Figure 10C:
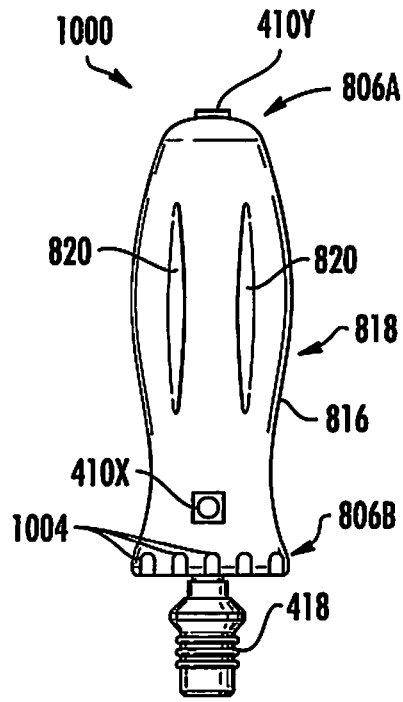
Figure 10D:
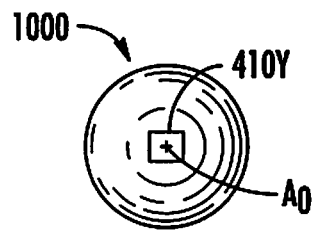
Figure 10E:
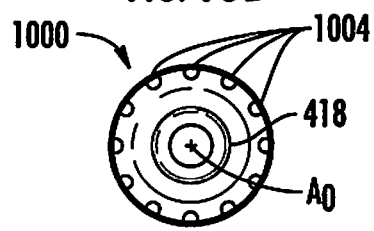

In yet another component of the multi-mode torque driver 118, the handle body 119 enables the user 126 to control the pedicle screw system 116 and also may facilitate an interrelationship between the battery 500, the anti-backdrive unit 408, adapter chuck 418, and the motor assembly 401, to operate as a cohesive system. The embodiment where the handle body 119 is a T-shaped body 120 will be discussed first. In this regard, FIGS. 7A through 7F are a top perspective view, front view, right side view, partial front view, top view, and bottom view, respectively, of the T-shaped body 120, wherein the switches 410X, 410Y are hidden from view. The T-shaped body 120 includes a center portion 532, the gripper handle portion 128, and an inner surface 535. The center portion 532 and the gripper handle portion 128 are collectively arranged in a capital letter "T" shape (FIG. 7B). The capital "T" shape enables the T-shaped body 120 to be more easily manipulated by the user 126 in the power mode 400A and the manual mode 400B, because the capital T-shape facilitates the output rotational axis A0 to be disposed within one of the interdigital spaces 405(2)-405(4) between the fingers 404(1)-404(4) and facilitates the feed force $F_F$ to be applied by the user 126 co-linearly with the output rotational axis A0 to minimize wobble. Specifically, the center portion 532 extends along the output rotational axis A0 from a first end 536A to a second end 536B, wherein the center portion 532 is arranged to transfer the manual torque $T_{MAN}$ applied by the user 126 at the gripper handle portion 128 from the first end 536A to the second end 536B. In this manner, when the multi-mode torque driver 118 is coupled to the pedicle screw 108(N2), then the center portion 532 may serve as a conduit for the manual torque $T_{MAN}$ to be transferred between the gripper handle portion 128 connected at the first end 536A and the anti-backdrive unit 408 disposed at the second end 536B.

The gripper handle portion 128 of the T-shaped body 120 serves as the interface for the user 126 during use of the multi-mode torque driver 118. The gripper handle portion 128 includes an external gripper surface 538 shaped as a plurality of protrusions 540A, 540B attached to and extending from the first end 536A of the center portion 532 to respective ones of the distal ends 542A, 542B disposed away from the output rotational axis A0. The protrusions 540A, 540B are adapted to receive and transfer the manual torque $T_{MAN}$ from the user 126 to the first end 536A of the center portion 532. The external gripper surface 538 is shaped for adjacent ones of the fingers 404(1)-404(4) of the user 126 (FIG. 4A) to wrap around respective ones of the protrusions 540A, 540B as the center portion 532 and the output rotational axis A0 are disposed between the adjacent ones of the fingers 404(1)-404(4) of the user 126 when the gripper handle portion 128 receives the manual torque $T_{MAN}$ from the user 126 in the manual mode 400B. In this manner, the user 126 may apply the manual torque $T_{MAN}$ during the manual mode 400B.

The distal ends 542A, 542B of the plurality of protrusions 540A, 540B are separated by a distance D3 (FIG. 4B) in a range from eighty (80) to one hundred forty (140) millimeters. The distance D3 may be configured to enable at least two fingers of the user 126 to be respectively wrapped around each of the respective ones of the protrusions 540A, 540B, in this way up to four of the four (4) fingers 404(1)-404(4) of the hand 422 of the user 126 may be engaged with the T-shaped body 120 during the manual mode 400B, so that the manual torque may be efficiently applied to the T-shaped body 120.

With continued discussion of the handle body 119, the center portion 532 includes a neck portion 533 (FIG. 5B) at the first end 536A having a width D4. The width D4 of the neck portion 533 may be sized to be less than twenty-five (25) millimeters to enable the neck portion 533 to be conveniently disposed in one of the interdigital spaces 405(2)-405(4) between the adjacent ones of the fingers 404(1)-404(4) during the power mode 400A and the manual mode 400B. The neck portion 533 is also configured as an enclosure to contain the electric motor 502 of the motor assembly 401. Disposing the electric motor 502 between the adjacent ones of the fingers 404(1)-404(4) provides the user 126 more precise control of the multi-mode torque driver 118 as the pedicle screw 108(N2) is guided along the desired axis A1, particularly when vibration is provided by the electric motor 502. The vibration is more effectively damped out by the user 126 by disposing the electric motor 502 between the adjacent ones of the fingers 404(1)-404(4). In this manner, the user 126 may more effectively avoid breaching external walls of the pedicle 208A (FIG. 2E) of the patient 104, wherein the breach may result in damage to the spinal cord 216 and/or the spinal nerves 218A, 218A' of the patient 104.

The center portion 532 also includes the bell portion 534 (FIG. 5B) at the second end 536B having a width D5. The bell portion 534 is configured to enclose the drive train 504 of the motor assembly 401 and thereby provide protection. The dimensions of the drive train 504 are provided to create the high torque and relatively slow rotational speed appropriate for managing pedicle screw attachments. Thus, the width D5 of the bell portion may be in a range from thirty (30) millimeters to eighty (80) millimeters. Further, the width D5 of the bell portion 534 is configured to enclose, protect and interface with the anti-backdrive unit 408. In this manner, the bell portion 534 facilitates operation of the motor assembly 401 and the anti-backdrive unit 408.

The inner surface 535 of the T-shaped body 120 enables components of the multi-mode torque driver 118 to be arranged within the T-shaped body 120 and provides the output opening 544 to transmit the motorized torque $T_{MOT}$ to outside of the T-shaped body 120 during the power mode 400A. In this regard, the inner surface 535 forms the output opening 544 through the second end 536B of the center portion 532. The handle body 119 may be an integral structure or may be a multi-component structure including a first end unit 545A, a medial unit 545B, a second end unit 545C, and the intermediate sleeve 513. At least one of the output element 414 of the anti-backdrive unit 408, the screw interface 122, and/or the adapter chuck 418 extends through the output opening 544 to transmit the motorized torque $T_{MOT}$ to the outside of the handle body 119. The output opening 544 may have a circular shape to better protect the anti-backdrive unit 408 by minimizing a gap between the handle body 119 and the at least one of the output element 414 of the anti-backdrive unit 408, the screw interface 122, and/or the adapter chuck 418. Consistent with this approach, the output opening 544 may have a maximum width D6 (FIG. 7F) less than half of an outer width D5 (FIG. 5B) of the second end 536B of the center portion 532. In the embodiment depicted in FIG. 5D the output element 414 extends through the output opening 544 to provide easier maintenance of the output element 414 of the anti-backdrive unit 408 in case the at least one locking elements 416(1)-416(N3) freeze in a locked position.

Moreover, the inner surface 535 of the handle body 119 also forms at least one motor control port 546A, 546B to enable control signals 548A, 548B to pass from the user 126 to the motor assembly 401. The control signals 548A, 548B may be mechanical or electronic signals that instruct the motor assembly 401 when to produce an amount of motorized torque $T_{MOT}$. In one embodiment, the handle body 119 may include the at least one switch 410X, 410Y disposed respectively at the at least one motor control port 546A, 546B to transmit the control signals 548A, 548B (FIG. 5D) through the at least one motor control port 546A, 546B. The switches 410X, 410Y may convert a mechanical motion from the user 126 to the control signals 548A, 548B. In the embodiment shown in FIG. 5D, the control signals 548A, 548B may travel from the switches 410X, 410Y to the electric motor 502 through electrically-conductive wires 550A, 550B. The motor control ports 546A, 546B may be disposed through the external through external gripper surface 538, and preferably at the distal ends 542A, 542B of the protrusions 540A, 540B. In this manner, the user 126 may efficiently control the operation of the motor assembly 401 with the hand 422.

Figure 5E:
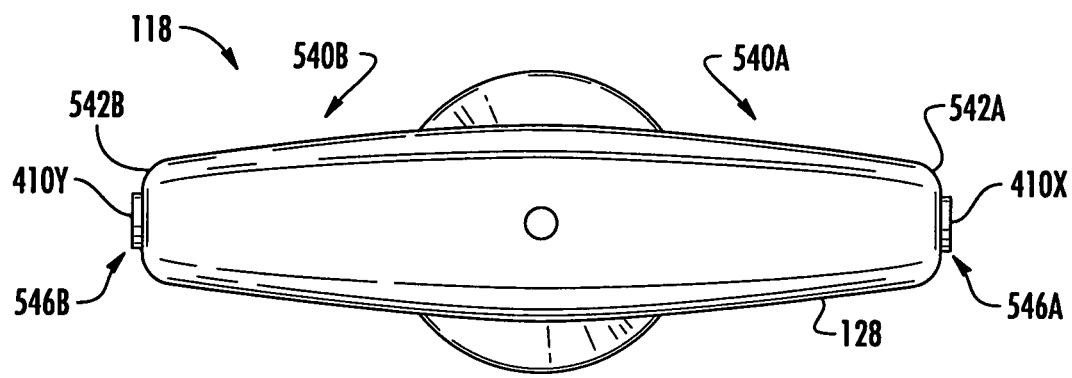
Figure 5F:
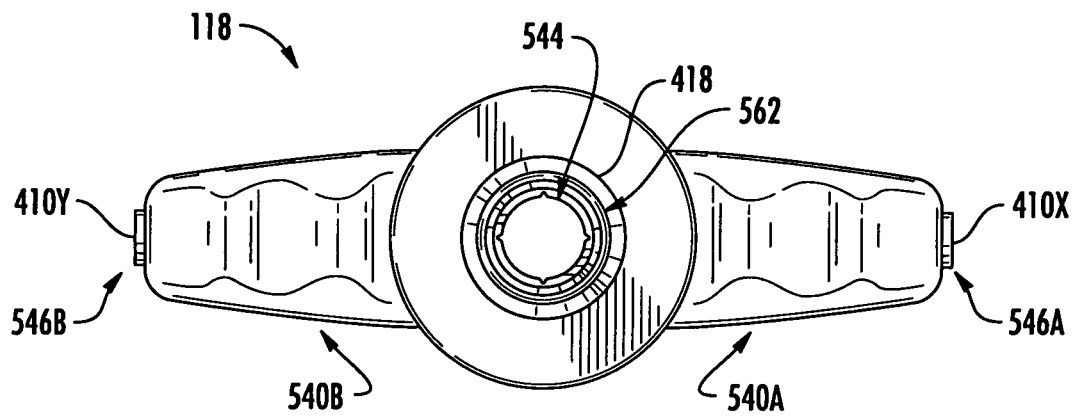
Figure 5G:
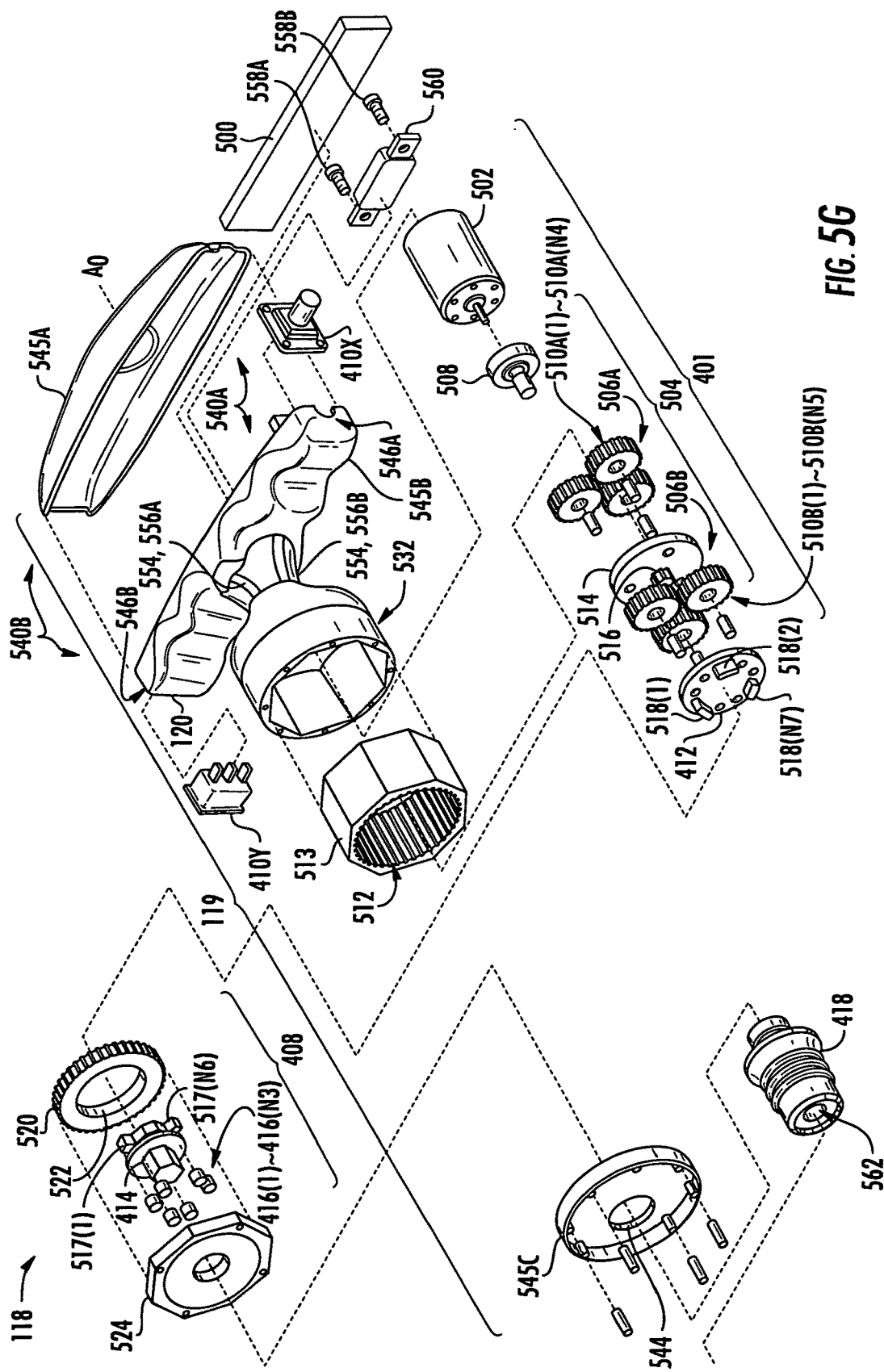
Figure 5H:
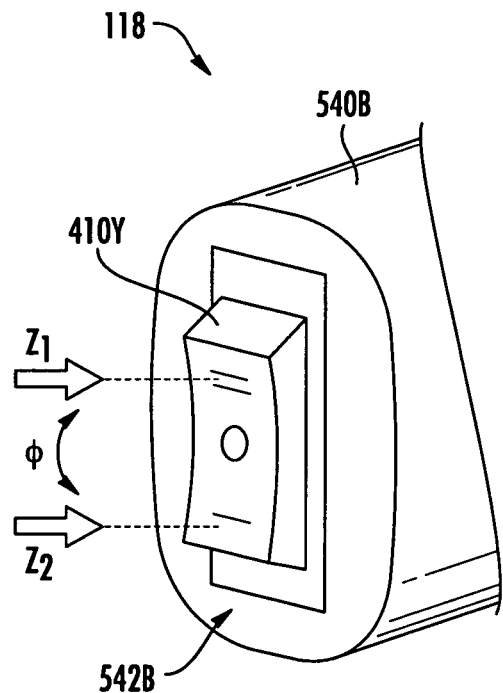
FIGS. 5H through 5I are left and right top perspective views, respectively, of switches at distal ends of protrusions of the T-shaped body of FIG. 5A through 5G.
Figure 5I:
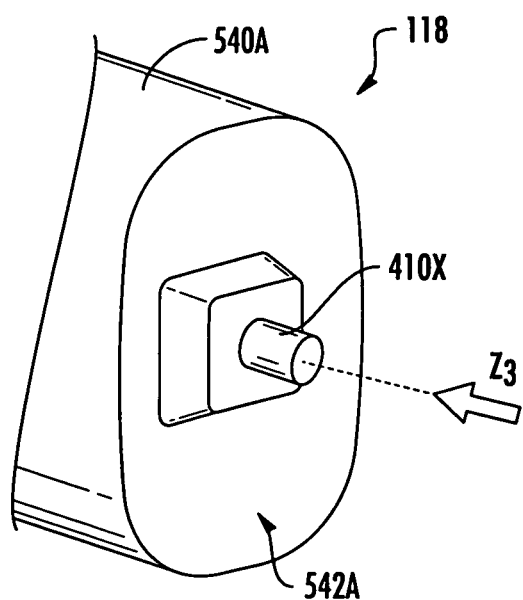

Also, the switches 410X, 410Y may operate cooperatively to control the generation of the motorized torque $T_{MOT}$. FIGS. 5H through 5I are left and right top perspective views, respectively, of the switches 410Y, 410X at the distal ends 542B, 542A of the protrusions 540B, 540A of the multi-mode torque driver 118 of FIG. 5A through 5G. The switch 410Y may be a rocker switch type as shown in FIG. 5H capable of rotating to three angular positions according to an angle Φ (phi) by forces Z1, Z2 applied by the user 126 to the switch 410Y. Each of the three angular positions may respectively designate for the motor assembly 401: a clockwise direction of the motorized torque, an off position, and a counterclockwise direction of the motorized torque $T_{MOT}$. The switch 410X may work in cooperation with the switch 410Y. The switch 410X may be a push button switch type configured to receive a force Z3 from the user 126. When the force Z3 is applied to the switch 410X and the switch 410Y designated either a clockwise or counterclockwise direction, then the motorized torque $T_{MOT}$ may be generated consistent with the direction designated by the switch 410Y. The switch 410X may be binary with only on and off positions corresponding to whether the force Z3 is applied. In other alternative embodiments the switch Z3 may control a level of the motorized torque $T_{MOT}$ based on an amount of the force Z3 applied to the switch 410X. In either case, the user 126 cannot use the switch 410X to generate the motorized torque $T_{MOT}$ while the switch 410Y is in the off position. Thus, the switches 410X, 410Y act cooperatively with each other. In this manner, the user 126 may use the switch 410Y to control a direction of the motorized torque $T_{MOT}$ or optionally place the motor assembly 401 in an off position to prevent inadvertent generation of the motorized torque $T_{MOT}$.

Further, the inner surface 535 of the handle body 119 also forms an inner space 552 (FIG. 7D) connecting the at least one of the motor control ports 546A, 546B and the output opening 544. The inner surface 535 includes a motor mounting interface 554 configured to receive the motorized torque $T_{MOT}$ from the electric motor 502 when the multi-mode torque driver 118 in a power mode 400A. The motor mounting interface 554 may include, for example, two fastener holes 556A, 556B in a wall of the center portion 532 within which at least one fastener 558A, 558B may secure the electric motor 502 to the handle body 119 using a motor backplate 560 (FIG. 5G). The motor backplate 560 may be attached to the electric motor 502 using, for example, an adhesive or a mechanical interface (not shown). Accordingly, when the motor backplate 560 is attached to the electric motor 502 and the motor backplate 560 is secured to the handle body 119, then the electric motor 502 is secured to the handle body 119. The motor mounting interface 554 may be arranged so that at least a portion of the electric motor 502 is disposed within the inner space 552 formed by the inner surface 535 in the center portion 532. In this manner, a greater percentage of the inner space 552 formed by the inner surface 535 within the protrusions 540A, 540B can be occupied by the battery 500, enabling battery types having higher discharge rates and/or energy capacities to be utilized.

The T-shaped body 120 may also facilitate the application of the $T_{MAN}$ by the user 126 in multiple revolutions of the pedicle screw 108(N2) comprising incremental applications each no more than one hundred eighty (180) degrees. The hand 422 of the user 126 is configured to conveniently apply the $T_{MAN}$ to the gripper handle portion 128 in angular ranges of one hundred eighty (180) or less. To avoid situations where the user 126 favors grasping only one of a front or a back of the gripper handle portion 128, the gripper handle portion 128 may be configured to have identical or substantially identical grasping experiences for the front and the back of the gripper handle portion 128. In order to make these experiences more similar, the T-shaped body 120 may include mirror symmetry or substantial mirror symmetry across two orthogonal geometric planes P3, P4 (FIGS. 5B and 5C), wherein the output rotational axis A0 is disposed within each of the two orthogonal geometric planes P3, P4. In this manner, the T-shaped body 120 may be configured to better receive applications of the manual torque $T_{MAN}$ to the T-shaped body 120 by the user 126.

Next, the adapter chuck 418 transmits the system torque T0 from the output element 414 of the anti-backdrive unit 408 to the screw interface 122. The adapter chuck 418 may be attached to and in rotational communication with the output element 414. The adapter chuck 418 may include a coupling opening 562 (FIG. 5F) that is concentric to the output rotational axis A0 and receives the standard connection end 300A of the screw interface 122, so that a coupling can occur to align the screw interface 122 with the output rotational axis A0. Within the coupling opening 562 the adapter chuck 418 may provide A0-type coupling compatibility or other standard coupling types (e.g., quarter inch square) to couple with the screw interface 122. It is also contemplated that the adapter chuck 418 may also include an adjustable ratchet feature (not shown) to transmit the system torque T0 in one selectable direction to minimize hand movement of the user 126 when applying the manual torque $T_{MAN}$ over multiple rotations. In this manner, the system torque may be conveyed to the pedicle screw 108(N2) via the adapter chuck 418.

Other embodiments of the handle body 119 are possible for use with the hand 422, of the user 126 to provide confidence to the user 126 that the pedicle screw attachment is strong and stable. In this regard, FIGS. 8A through 8G are a top perspective view, front view, left side view, sectional front view, top view, bottom view, and exploded view, respectively, of a second exemplary embodiment of a multi-mode torque driver 800 compatible with the screw interface 122 of FIG. 1B, wherein a handle body 119 in this second embodiment is an axially-shaped body 802 with a flared end 804. The multi-mode torque driver 800 and the axially-shaped body 802 operate similarly to the multi-mode torque driver 118 and the T-shaped body 402, respectively, accordingly only the differences will be discussed for purposes of clarity and conciseness.

The axially-shaped body 802 embodiment of the handle body 119 extends from a first end 806A to a second end 806B along the rotational axis A0. The axially-shaped body 802 may be an integral structure or may be a multi-component structure (FIG. 8G) coupled together, for example with fasteners, and including a first end unit 803A at the first end 806A, a second end unit 803C at the second end 806B, a medial unit 803B disposed between the first end unit 803A and the second end unit 803C, and the intermediate sleeve 513. An inner surface 808 of the axially-shaped body 802 forms an inner space 810 of the axially-shaped body 802 and connects an output opening 812 of the axially-shaped body 802 to at least one motor control ports 814A, 814B. The multi-mode torque driver 800 may also include the motor assembly 401, the anti-backdrive unit 408, and the battery 500, and the adapter chuck 418. The inner space 810 may contain the motor assembly 401, the anti-backdrive unit 408, and the battery 500. The motor assembly 401 and the anti-backdrive unit 408 may interact and be coupled to the inner surface 808 in an analogous manner as they interact and are coupled with the inner surface 535 of the multi-mode torque driver 118. The output opening 812 may be disposed at the second end 806B of the axially-shaped body 802 and be concentric with the output rotational axis A0 for protection of the anti-backdrive unit 408. In this manner, the system torque T0 may be communicated to the adapter chuck 418 through the output opening 812.

The multi-mode torque driver 800 operates in the power mode 400A and the manual mode 400B in a similar manner as the multi-mode torque driver 118 and the method 450. The axially-shaped body 802 includes an axial gripper surface 816 disposed between the first and the second ends 806A, 806B. The axial gripper surface 816 may be disposed to surround the output rotational axis A0, so when grasped in a "fist grip" by the hand of the user 126 as depicted in FIG. 8B, the fingers 404(1)-404(4) are wrapped at least partially around and abut against the axially-shaped body 802 in one angular direction with the interdigital spaces 405(2)-405(4) between the fingers 404(1)-404(4) of the user 126 closed or substantially closed as the thumb 403 is wrapped at least partially around the axially-shaped body 802 in the opposite angular direction as the fingers 404(1)-404(4) are wrapped. In this manner, the fingers 404(1)-404(4), the thumb 403, and the palm 420 of the hand 422 of the user may abut against the axial gripper surface 816. When abutted against the axial gripper surface 816, the hand 422 of the user 126 may utilize the abutment to support the axially-shaped body 802 in the power mode 400A, apply the manual torque $T_{MAN}$ in the manual mode 400B and receive the resistance torque $T_R$ in the manual mode 400B. The "fist position" may provide a lessened sensitivity to the resistance torque $T_R$ as discussed above for the T-shaped body 120, because the resistance torque is received parallel or substantially parallel to the thumb 403 and the fingers 404(1)-404(4) as opposed to substantially orthogonal thereto. However, the absence of the protrusions 540A, 540B enables the axially-shaped body 802 to have a more compact shape which may be more appropriate when the user 126 requires additional space for other surgical tasks or medical equipment. In this manner, the resistance torque $T_R$ may be monitored during the manual mode 400B to determine whether the pedicle screw attachment is strong and stable.

It is noted that the axial gripper surface 816 may include a convex portion 818 to better interface with the palm 420 of the user 126. The convex portion 818 may also include at least one medial groove 820 to reduce slippage with the fingers 404(1)-404(4) and the palm 420 during application of the manual torque $T_{MAN}$. The axial gripper surface 816 may also include the flared end 804 at the second end 806B of the axially-shaped body 802. The flared end 804 may facilitate efficient positioning of the thumb 403 during operation. In this manner, the axial gripper surface 816 may be shaped for efficient use during the power mode 400A and the manual mode 400B.

The user 126 may control the generation of the motorized torque $T_{MOT}$ to be transmitted to the anti-backdrive unit 408 in the power mode 400A by use of the switches 410X, 410Y. The switches 410X, 410Y may function analogously as with both the multi-mode torque drivers 118, 800 to generate the motorized torque $T_{MOT}$, however, the locations may be different. In this regard, the switches 410Y, 410X may be respectively disposed at the motor control ports 814A, 814B at the first and the second ends 806A, 806B. The motor control port 814A may be disposed at the rotational axis A0 and first end 806A to avoid inadvertent contact between the switch 410Y and the hand 422 when the manual torque $T_{MAN}$ is being applied to the axially-shaped body 802. In contrast, the motor control port 814B may be disposed at the second end 806B and at or near the axial gripper surface 816. The location of the motor control port 814B may be disposed to facilitate convenient contact between the switch 410X and the thumb 403 to generate the motorized torque $T_{MOT}$ during the power mode 400A.

Other embodiments of the handle body 119 are possible. FIGS. 9A through 9E are a top perspective view, front view, left side view, top view, and bottom view, respectively, of a third exemplary embodiment of a multi-mode torque driver 900 compatible with the screw interface 122 of FIG. 1B, wherein the handle body 119 in this second embodiment is an second axially-shaped body 902 with a second flared end 904. The second axially-shaped body 902 of the multi-mode torque driver 900 is similar to the axially-shaped body 802 of the multi-mode torque driver 800, and so only major differences are discussed. The second flared end 904 may be disposed at the first end 806A of the second axially-shaped body 902 to form an abutment with the palm 420 of the user 126. In this manner, the second flared end 904 facilitates the positioning of the hand 422 during the power mode 400A and the manual mode 400B for more precise management of the pedicle screw attachment 109(N2).

Other embodiments of the handle body 119 are possible. FIGS. 10A through 10E are a top perspective view, front view, left side view, top view, and bottom view, respectively, of a fourth exemplary embodiment of a multi-mode torque driver 1000 compatible with the screw interface of FIG. 1B, wherein the handle body 119 in this fourth embodiment is a third axially-shaped body 1002 with a flared end grooves 1004. The third axially-shaped body 1002 of the multi-mode torque driver 1000 is similar to the axially-shaped body 802 of the multi-mode torque driver 800, and so only major differences are discussed. The flared end grooves 1004 may be disposed as part of the flared end 804. The thumb 403 may abut against the flared end grooves 1004 during the application of the manual torque $T_{MAN}$ during the manual mode 400B to decrease slippage between the hand 422 and the multi-mode torque driver 1000. In this manner, the manual torque $T_{MAN}$ may be more efficiently applied by the user 126.

Many modifications and other embodiments not set forth herein will come to mind to one skilled in the art to which the embodiments pertain having the benefit of the teachings presented in the foregoing descriptions and the associated drawings. Therefore, it is to be understood that the description and claims are not to be limited to the specific embodiments disclosed and that modifications and other embodiments are intended to be included within the scope of the appended claims. For example, the multi-mode torque driver 118 may be used when coupled to a tap drill to tap the desired trajectory A1 of the pedicle screw 108(N2) before the pedicle screw 108(N2) is inserted into the vertebra 102(N1). It is intended that the embodiments cover the modifications and variations of the embodiments provided they come within the scope of the appended claims and their equivalents. Although specific terms are employed herein, they are used in a generic and descriptive sense only and not for purposes of limitation.

What is claimed is:
1. A multi-mode torque driver for managing a pedicle screw attachment with a vertebra, comprising:
 a handle body extending along an output rotational axis from a first end to a second end, the handle body including an inner surface forming an inner space connecting at least one motor control port to an output opening at the second end, wherein the handle body includes a center portion connecting the first end to the second end, the handle body further includes a gripper handle portion formed of a plurality of protrusions attached to the center portion at the first end of the handle body and forming a T-shaped body collectively with the center portion, the plurality of protrusions extend from the first end to distal ends disposed away from the output rotational axis, wherein the gripper handle portion is shaped for adjacent fingers of a single hand of a user to wrap around respective ones of the plurality of protrusions as the center portion and the output rotational axis are disposed within an interdigital space between the adjacent fingers when the gripper handle portion receives a manual torque from the user in a manual mode;

a motor assembly disposed within the inner space and generating a motorized torque at an output interface of the motor assembly during a power mode; and an anti-backdrive unit coupled to the motor assembly and including:
an output element disposed through the output opening, at least one locking element, and
a housing portion statically coupled to the inner surface of the handle body at the second end of the handle body and the housing portion including an inner circumferential surface, wherein the anti-backdrive unit is disposed within the inner space, wherein the at least one locking element, the output element, and the output interface of the motor assembly are commonly rotatable about the output rotational axis and disposed within the housing portion, wherein upon the output element of the anti-backdrive unit receiving the motorized torque from the motor assembly in the power mode as a system torque, the output element rotates and the output interface of the motor assembly abuts against the at least one locking element to move the at least one locking element along the inner circumferential surface, and wherein upon the manual torque being applied to the handle body by the single hand of the user while the output element is coupled to a pedicle screw and the output element is free from the motorized torque, then the manual torque moves the handle body relative to the output element until the at least one locking element abuts against both the inner circumferential surface of the housing portion and a non-concentric external surface of the output element to create a mechanical interference which automatically locks the output element relative to the handle body and transmits the manual torque from the handle body to the output element as the system torque in the manual mode.

2. The multi-mode torque driver of claim 1, wherein the motor assembly in the power mode is configured to generate the motorized torque in a range from two (2) Newton-meters to ten (10) Newton-meters, and generate a rotational speed in a second range from fifty (50) RPM to two-hundred (200) RPM.

3. The multi-mode torque driver of claim 1, wherein the motor assembly includes at least one epicyclic gear train stage having a collective a gear ratio in a range from 80:1 to 140:1.

4. The multi-mode torque driver of claim 1, further comprising at least one switch disposed at the at least one motor control port and the at least one switch comprising a plurality of non-zero speed positions.

5. The multi-mode torque driver of claim 4, wherein the at least one switch includes a rocker switch comprising the plurality of non-zero speed positions for the user to respectively select clockwise and counterclockwise directions of the motorized torque.

6. The multi-mode torque driver of claim 1, wherein the at least one motor control port is disposed at one or more of the distal ends.

7. The multi-mode torque driver of claim 1, further comprising a battery disposed within the gripper handle portion, wherein the battery is arranged to power the motor assembly during the power mode.

8. The multi-mode torque driver of claim 1, wherein the handle body further includes an axial gripper surface connecting the first and the second ends, the axial gripper surface encloses the output rotational axis, wherein the axial gripper surface is shaped for fingers and a thumb of the single hand to be wrapped at least partially around the axial gripper surface in opposite directions with the output rotational axis disposed within an interdigital space between the thumb and at least one of the fingers of the single hand when the axial gripper surface receives the manual torque from the user in the manual mode.

9. The multi-mode torque driver of claim 1, wherein the output element of the anti-backdrive unit receives the motorized torque from the output interface of the motor assembly through the at least one locking element during the power mode.

10. The multi-mode torque driver of claim 1, wherein the gripper handle portion includes mirror symmetry or substantial mirror symmetry across two orthogonal geometric planes, wherein the output rotational axis is disposed within each of the two orthogonal geometric planes.

11. The multi-mode torque driver of claim 1, wherein the gripper handle portion is shaped to abut against a palm of the single hand of the user to receive a feed force from the user, wherein the feed force is applied co-linear with the output rotational axis.

12. The multi-mode torque driver of claim 1, wherein the output opening has a maximum width less than half of an outer width of the second end of the handle body.

13. The multi-mode torque driver of claim 1, further comprises a neck portion of the center portion disposed at the first end of the handle body, wherein the neck portion is configured to be disposed in the interdigital space between the adjacent fingers of the user.

14. The multi-mode torque driver of claim 13, wherein the distal ends of the plurality of protrusions are separated by a distance that is in a range from eighty (80) to one hundred forty (140) millimeters.

15. The multi-mode torque driver of claim 14, further comprising a bell portion of the center portion of the T-shaped body disposed at the second end, wherein a width of the bell portion is in a second range from thirty (30) millimeters to eighty (80) millimeters.

16. A method for managing a pedicle screw attachment with a vertebra, comprising:
transmitting, with an output element of an anti-backdrive unit disposed within an inner space of a handle body of a multi-mode torque driver, a system torque from the output element to a pedicle screw, wherein the system torque includes a manual torque during a manual mode and a motorized torque during a power mode, wherein the system torque moves the pedicle screw relative to a vertebra, and the handle body extending along an output rotational axis from a first end to a second end, the handle body including an inner surface forming the inner space connecting at least one motor control port to an output opening at the second end, wherein the handle body is formed as a T-shaped body and the transmitting the manual torque includes conveying the manual torque from a gripper handle portion of the T-shaped body to a center portion of the T-shaped body at the second end, wherein the center portion extends along the output rotational axis from the first end to the second end, wherein the anti-backdrive unit is coupled to the center portion at the second end, and the gripper handle portion is formed from a plurality of protrusions attached to and extending from the first end;

generating, with a motor assembly disposed within the inner space, the motorized torque at an output interface of the motor assembly during the power mode, wherein the motor assembly is coupled to the anti-backdrive unit, wherein the anti-backdrive unit includes the output element disposed through the output opening, at least one locking element, and a housing portion statically coupled to the inner surface of the handle body at the second end of the handle body and the housing portion including an inner circumferential surface;

upon receiving the motorized torque with the output element of the anti-backdrive unit from the output interface of the motor assembly during the power mode as the system torque, the output element rotates and the output interface of the motor assembly abuts against the at least one locking element to move the at least one locking element along the inner circumferential surface of the housing portion, wherein the at least one locking element, the output element, and the output interface commonly rotate about the output rotational axis; and upon applying the manual torque to the handle body with a single hand of a user while the output element is coupled to the pedicle screw and the output element is free from the motorized torque, then the manual torque moves the handle body relative to the output element until the at least one locking element abuts against both the inner circumferential surface of the housing portion and a non-concentric external surface of the output element to create a mechanical interference which automatically locks the output element relative to the handle body and transmits the manual torque from the handle body to the output element as the system torque in the manual mode.

17. The method of claim 16, further comprising transitioning from the manual mode to the power mode based on an amount of resistance torque received by the user via the handle body during the manual mode.

18. The method of claim 16, further comprising monitoring a strength of an attachment of the pedicle screw to the vertebra by transitioning from the power mode to the manual mode and evaluating the strength based on an amount of resistance torque received by the user via the handle body during the manual mode.

19. The method of claim 16, wherein the applying the manual torque with the single hand of the user includes grasping the gripper handle portion of the T-shaped body with the output rotational axis disposed within an interdigital space between adjacent fingers of the single hand.

20. The method of claim 16, wherein the applying the manual torque includes applying a feed force along the output rotational axis by abutting a palm of the single hand against an external gripper surface of the gripper handle portion with the output rotational axis intersecting the palm.

21. The method of claim 16, wherein the generating the motorized torque includes the motorized torque in a range from two (2) Newton-meters to ten (10) Newton-meters, and during the power mode the output element rotates about the output rotational axis at a speed in a second range from fifty (50) RPM to two hundred (200) RPM.

22. The method of claim 16, further comprising selecting a direction of the motorized torque, with at least one switch of the multi-mode torque driver, wherein the at least one switch comprises a plurality of non-zero speed positions corresponding to the direction of the motorized torque including a clockwise direction and a counterclockwise direction.

23. The multi-mode torque driver of claim 13, wherein the neck portion has a width less than twenty-five (25) millimeters.

24. The method of claim 16, wherein the receiving the motorized torque with the output element of the anti-backdrive unit from the motor assembly during the power mode includes the output element of the anti-backdrive unit receiving the motorized torque from the output interface of the motor assembly through the at least one locking element during the power mode.

* * * * *